(12) United States Patent
Summers et al.

(10) Patent No.: US 9,131,919 B2
(45) Date of Patent: *Sep. 15, 2015

(54) VERSATILE BREAST ULTRASOUND SCANNING

(71) Applicant: U-Systems, Inc., Sunnyvale, CA (US)

(72) Inventors: Douglas G. Summers, Palo Alto, CA (US); Shih-Ping Wang, Los Altos, CA (US); Jiayu Chen, Palo Alto, CA (US); Tor C. Anderson, Mountain View, CA (US)

(73) Assignee: U-Systems, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/623,760

(22) Filed: Sep. 20, 2012

(65) Prior Publication Data

US 2014/0066771 A1 Mar. 6, 2014

Related U.S. Application Data

(63) Continuation of application No. 11/587,078, filed as application No. PCT/US2005/014321 on Apr. 26, 2005, now abandoned.

(60) Provisional application No. 60/565,698, filed on Apr. 26, 2004, provisional application No. 60/577,078, filed on Jun. 4, 2004, provisional application No. 60/629,007, filed on Nov. 17, 2004.

(51) Int. Cl.
| | |
|---|---|
| *A61B 8/13* | (2006.01) |
| *A61B 8/08* | (2006.01) |
| *A61B 8/00* | (2006.01) |

(52) U.S. Cl.
CPC .............. *A61B 8/0825* (2013.01); *A61B 8/406* (2013.01); *A61B 8/4218* (2013.01);
(Continued)

(58) Field of Classification Search
CPC .... A61B 8/0825; A61B 8/406; A61B 8/4218; A61B 8/4281; A61B 8/4405

USPC ................... 600/437, 443, 448, 459; 382/128
See application file for complete search history.

(56) References Cited

U.S. PATENT DOCUMENTS

| | | | |
|---|---|---|---|
| 3,964,296 A | 6/1976 | Matzuk | |
| 3,971,950 A | * 7/1976 | Evans et al. | ..................... 378/37 |

(Continued)

FOREIGN PATENT DOCUMENTS

| | | |
|---|---|---|
| DE | 3222053 A1 | 12/1983 |
| DE | 19753571 A1 | 6/1999 |
| DE | 19902521 A1 | 7/2000 |

OTHER PUBLICATIONS

Foster F. S. et al. "The Ultrasound Macroscope: Initial Studies of Breast Tissue" Ultrasonic Imaging USA, vol. 6, No. 3, Jul. 1984, pp. 243-261.

(Continued)

*Primary Examiner* — Baisakhi Roy
(74) *Attorney, Agent, or Firm* — Alleman Hall McCoy Russell & Tuttle LLP

(57) ABSTRACT

Versatile ultrasound scanning of a breast is described using an apparatus (1202) including a hand-manipulable compression/scanning assembly (1208). The compression/scanning assembly (1208) comprises an ultrasound transducer (1304) and a compressive member comprising an at least partially conformable membrane (1218) in a substantially taut state, the membrane (1218) having a first surface compressing the breast in a generally chestward direction and a second surface opposite the first surface. The compression/scanning assembly (1208) further comprises a transducer translation mechanism coupled to the ultrasound transducer (1304) and configured to sweep the ultrasound transducer across the second surface of the membrane to scan the breast while compressed in the generally chestward direction. Systemized and/or standardized ultrasonic scanning of a breast based on hand-manipulable scanners (1208, 1508) having substantially planar scanning surfaces is also described.

17 Claims, 25 Drawing Sheets

(52) U.S. Cl.
CPC .............. *A61B 8/4405* (2013.01); *A61B 8/483* (2013.01); *A61B 8/4281* (2013.01); *A61B 8/4455* (2013.01); *A61B 8/4472* (2013.01); *A61B 8/461* (2013.01); *A61B 8/467* (2013.01)

(56) References Cited

U.S. PATENT DOCUMENTS

| | | | | |
|---|---|---|---|---|
| 4,130,112 | A * | 12/1978 | Frazer | 600/448 |
| 4,186,747 | A | 2/1980 | Iinuma | |
| 4,485,819 | A | 12/1984 | Igl | |
| 4,545,385 | A | 10/1985 | Pirschel | |
| 5,833,627 | A * | 11/1998 | Shmulewitz et al. | 600/562 |
| 7,278,991 | B2 * | 10/2007 | Morris et al. | 606/41 |
| 7,615,008 | B2 * | 11/2009 | Zhang et al. | 600/437 |
| 7,625,371 | B2 * | 12/2009 | Morris et al. | 606/41 |
| 7,806,827 | B2 * | 10/2010 | Zhang et al. | 600/459 |
| 7,828,733 | B2 * | 11/2010 | Zhang et al. | 600/437 |
| 2002/0120260 | A1 * | 8/2002 | Morris et al. | 606/41 |
| 2003/0007598 | A1 * | 1/2003 | Wang et al. | 378/37 |
| 2003/0167004 | A1 * | 9/2003 | Dines et al. | 600/437 |
| 2004/0010193 | A1 * | 1/2004 | Entrekin et al. | 600/437 |
| 2004/0181152 | A1 * | 9/2004 | Zhang et al. | 600/437 |
| 2005/0080333 | A1 * | 4/2005 | Piron et al. | 600/417 |
| 2005/0245826 | A1 * | 11/2005 | Gervais | 600/443 |
| 2007/0016003 | A1 * | 1/2007 | Piron et al. | 600/415 |
| 2012/0172704 | A1 * | 7/2012 | Piron et al. | 600/410 |

OTHER PUBLICATIONS

European Search Report dated Jan. 29, 2007 in connection with European Patent Application No. 03 73 4336.

* cited by examiner

VERSATILE BREAST ULTRASOUND SCANNING

CROSS-REFERENCE TO RELATED APPLICATIONS

This application is a continuation of U.S. patent application Ser. No. 11/587,078, filed Jun. 18, 2008 which in turn is a U.S. national stage application under 35 U.S.C. 371 of PCT International Application No. PCT/US2005/14321, filed Apr. 26, 2005, which claims the benefit of U.S. Provisional Application No. 60/565,698, filed Apr. 26, 2004, U.S. Provisional Application No. 60/577,078, filed Jun. 4, 2004, and U.S. Provisional Application No. 60/629,007, filed Nov. 17, 2004, the entire contents of each of which are incorporated by reference herein.

FIELD

This provisional patent specification relates to medical ultrasound imaging. More particularly, the present specification relates to a versatile breast ultrasound scanning apparatus and related methods.

BACKGROUND

Volumetric ultrasound scanning of the breast has been proposed as a complementary modality for breast cancer screening as described, for example, in the commonly assigned US 2003/007598A1 published Jan. 9, 2003, which is incorporated by reference herein. Whereas a conventional two-dimensional x-ray mammogram only detects a summation of the x-ray opacity of individual slices of breast tissue over the entire breast, ultrasound can separately detect the sonographic properties of individual slices of breast tissue, and therefore may allow detection of breast lesions where x-ray mammography alone fails. Another well-known shortcoming of x-ray mammography practice is found in the case of dense-breasted women, including patients with high content of fibroglandular tissues in their breasts. Because fibroglandular tissues have higher x-ray absorption than the surrounding fatty tissues, portions of breasts with high fibroglandular tissue content are not well penetrated by x-rays and thus the resulting mammograms contain reduced information in areas where fibroglandular tissues reside.

The commonly assigned WO 2004/030523A2 published on Apr. 15, 2004, which is incorporated by reference herein, describes a full-field breast ultrasound (FFBU) scanning apparatus that compresses a breast along view plane such as the craniocaudal (CC) plane, the mediolateral oblique (MLO) plane, etc., and ultrasonically scans the breast. A scanning surface comprises an at least partially conformable, substantially taut membrane or film sheet compressing one side of the breast. The other side of the breast is compressed by a compression plate with an inflatable air bladder. A transducer translation mechanism holds a transducer surface against an opposite side of the film sheet while translating the transducer thereacross to scan the breast. An irrigation system automatically maintains a continuous supply of coupling agent at an interface between the transducer surface and the film sheet as the transducer is translated.

The operation of the scanning apparatus described in WO 2004/030523A2, supra, depends at least in part on the "pendulous" properties of the breast, that is, the ability of the breast to extend away from the chest wall onto the scanning surface for compression along the axial plane (for CC scan), sagittal plane (for lateral scan), or other anti-coronal plane lying between the axial and sagittal planes (e.g., for MLO scan). As used herein, the term anti-coronal plane refers to a plane that lies generally perpendicular to the coronal plane. As with conventional x-ray mammography, the presumption is made that most breasts will have such pendulous properties. While effective for a large portion of the population, problems arise for patients having smaller breasts without pendulous properties, because much of the diagnostically relevant breast tissue cannot extend outward over the scanning surface by a sufficient amount. Moreover, even for patients with pendulous breasts, there can be difficulty in imaging the tissue near the chest wall that does not extend onto the scanning surface.

One important quality a breast ultrasound scanning apparatus is ease of mechanical control and manipulation. Generally speaking, acquiring volumetric ultrasonic breast scans can be a highly patient-specific process, not only in view of the wide variety of breast sizes, shapes, and densities, but also in view of the wide variety of different patient body shapes near and around the breast area (e.g., shoulder contours, sternum contours, ribs contours, etc.) A scanning apparatus that is versatile and easily adaptable to the particular patient being scanned can therefore facilitate optimal acquisition of ultrasonic views of the breast volume. Moreover, ease of use can also positively affect the salability and commercial success of the scanning apparatus.

In addition to being able to perform thorough and high-quality volumetric scans of breasts having different sizes, shapes, and densities, which requires substantial scanner versatility, another important quality in a breast scanning system is its amenability to at least some degree of clinical systemization and/or standardization. For example, it would be desirable to have the same breast scanned the same way in different years to provide meaningful year-over-year comparisons, even where the ultrasound scans are performed by different technicians on different scanning units. Likewise, it would be desirable to provide a system that allows for easy comparisons of tissue structures in different patients having similarly-formed breasts, to foster more universally applicable radiologist interpretation skills, to provide for the development of better training materials, and/or to provide for the development of image databases for training automated or semi-automated computer-aided diagnosis (CAD) systems.

Accordingly, it would be desirable to provide a breast ultrasound scanning system that is capable of accommodating small, non-pendulous breasts as well as pendulous breasts.

It would be further desirable to provide a breast ultrasound scanning apparatus that can achieve high-quality ultrasound imaging even near the chest wall of the patient.

It would be even further desirable to provide such a breast ultrasound scanning apparatus that is comfortable for the patient, has a cost-efficient patient throughput rate, and that is cost-efficient to own even for smaller medical clinics.

It would be still further desirable to provide such a breast ultrasound scanning apparatus that is versatile, able to accommodate patients of different heights and/or disabilities, and capable of facilitating individualized scanning procedures.

It would be even further desirable to provide methods for facilitating at least some degree of standardization in the way breasts of different sizes, shapes, and/or densities are scanned using such breast ultrasound scanning apparatus.

SUMMARY

According to one preferred embodiment, an apparatus and related methods for full-field breast ultrasound (FFBU) scanning of a breast of a patient are provided, the apparatus having an ultrasound transducer with a scanning surface, a first compressive member comprising an at least partially conformable membrane in a substantially taut state, the membrane having a first surface for contacting the breast and a second surface opposite the first surface, a second compressive member movable relative to the first compressive member to allow placement and compression of the breast therebetween, and a transducer translation mechanism configured to hold the scanning surface of the ultrasound transducer against said second surface of the membrane while translating the ultrasound transducer thereacross to scan the breast. Methods similar to those described in WO 2004/030523A2, supra, are used to obtain scans if the breast is to be compressed along a CC, MLO, or other anti-coronal plane. However, according to a preferred embodiment, the apparatus is also adapted to accommodate head-on scans of a chestwardly-compressed breast through (i) positioning of the first compressive member to receive the breast in a head-on fashion and compression of the breast in a chestward direction, and (ii) removal of the second compression plate, or movement of the second compression plate to an out-of-the-way location.

Preferably, the FFBU scanning apparatus comprises a rigid and substantially stationary frame, and the first and second compressive members are pivotably connected to an arm that is, in turn, pivotably mounted to the frame. This allows for increased flexibility in the number of ways the patient and technician may be disposed around the FFBU apparatus while the scans are taking place. It also can accommodate tall patients, short patients, patients in wheelchairs or having other disabilities. In one preferred embodiment, the arm may be mounted to the frame in a turret-like configuration, and the first and second compressive members are pivotably connected to the arm at sockets having ball-joint characteristics.

According to another preferred embodiment, the FFBU scanning apparatus is integrated with a conventional ultrasound system and provided with a conventional user interface having a hand-held ultrasound probe. This provides for high versatility of the FFBU scanning apparatus, allowing for miscellaneous manual breast scans by the physician for any of a variety of reasons. For small clinics, the small footprint of the FFBU scanning apparatus allow it to double as a conventional ultrasound machine for general use (e.g., pregnancy, vascular, thoracic scans) as well as an FFBU scanner.

According to another preferred embodiment, a gel pad is integrated onto the surface of the first compressive member, the gel pad promoting improved patient comfort while also promoting better acoustic coupling with a chestwardly-compressed breast for head-on scans. Optionally, the second compressive member can be permanently removed and the FFBU scanning apparatus can serve just as a head-on scanner. The FFBU scanning apparatus is adapted and configured to allow for head-on breast scanning in a variety of positions including prone, standing while leaning forward, standing upright, partially supine, and fully supine positions.

According to another preferred embodiment, an apparatus and related methods for full-field breast ultrasound (FFBU) scanning of a breast of a patient are provided, the apparatus at least partially compressing the breast in a generally chestward direction and acquiring scans thereof. The apparatus is particularly useful for patients in fully supine positions or partially supine (i.e., reclining) positions, although it may be used on upright patients as well. The apparatus comprises a compression/scanning assembly having an at least partially self-contained, pod-like character that is adapted for easy manipulation by a user. The compression/scanning assembly comprises an ultrasound transducer and an at least partially conformable membrane in a substantially taut state, the membrane having a first surface for contacting the breast and a second surface opposite the first surface, the transducer being swept across the second surface in contact therewith to scan the breast.

In one preferred embodiment, the compression/scanning assembly is maintained at an end of a movable support arm that is, in turn, coupled to a frame. The end of the support arm has all three translational degrees of freedom (e.g., x, y, and z) relative to the frame, and the compression/scanning assembly has all three rotational degrees of freedom (e.g., pitch, roll, and yaw) relative to the end of the movable support arm. Preferably, the support arm supports the compression/scanning assembly in a springable, partially frictionable manner to be either (i) neutrally buoyant in space, or (ii) to have a light net downward weight (e.g., 2-3 pounds) for breast compression, while allowing for easy user manipulation. In addition to being easy to manipulate, the scanning apparatus further promotes patient comfort and reliable scanning because the patient can comfortably breathe during the procedure without confounding the scanning results, because the compression/scanning assembly rises up and down (or in and out) with the patient's chest. Optionally, the support arm may comprise potentiometers to allow position and orientation sensing for the compression/scanning assembly, or other types of position and orientation sensing (e.g., gyroscopic, magnetic, optical) can be used. Further position and orientation sensors can optionally be placed on the patient's chest to detect relative motion between the compression/scanning assembly and the patient, where desired.

In one preferred embodiment, the compression/scanning assembly comprises a housing within which the transducer is disposed, the housing including an aperture across which the membrane is positioned. Preferably, both the membrane and the housing are transparent at locations that allow the user to view the breast surface through the compression/scanning assembly during the positioning and scanning process. In one preferred embodiment, a lateral support element is provided extending from the membrane toward the breast for gentle lateral confinement of the breast during the scans, the lateral support element comprising an at least partially pliable material such as a rubber material.

In another preferred embodiment, the compression/scanning assembly is mechanically separated from the support arm, being fully supported and manipulated by the user's hands. Optionally, the compression/scanning assembly may be electrically coupled to an ultrasound processor through a cable extending from the support arm, the cable also providing backup support by suspending the compression/scanning assembly above the floor in case it is accidentally released by the user. In still other preferred embodiments, the compression/scanning assembly uses wireless digital communications or other electromagnetic radiation-based communications to transfer signals to the ultrasound processor.

Also provided is a method for ultrasonically scanning a breast using a pod-like, hand-manipulable ultrasound scanner including an ultrasound transducer and having a substantially flat compressive surface, the compressive surface contacting the breast on a first side, an ultrasound transducer being swept across a second side of the compressive surface. In one preferred embodiment, a single head-on scan is taken for each breast, the compressive surface being substantially parallel to a coronal plane and chestwardly pressed against the breast. In another preferred embodiment, a plurality of ancillary compressive scans of each breast is acquired for which the compressive surface is oriented in a respective plurality of predetermined off-coronal planes. In one embodiment, the image volumes acquired from the ancillary compressive scans are used to supplement the image volume acquired from the head-on scan. In another embodiment, the single head-on scans are omitted and only the image volumes acquired from the ancillary compressive scans are used. The ancillary compressive scans can include, but are not limited to, a lateral frontal scan, a medial frontal scan, an inferior frontal scan, and a superior frontal scan.

In one embodiment, the number and selection of ancillary compressive scans is determined according to a size category of the breast. For a small breast, the lateral frontal scan and the medial frontal scan can suffice to ultrasonically image the clinically relevant tissues. For a medium sized breast, the inferior frontal scan is additionally acquired to facilitate sufficient imaging of the clinically relevant tissues. For a large-sized breast, both the inferior frontal scan and the superior frontal scan are additionally acquired for capturing the clinically relevant tissues. Advantageously, a set of generally standard and comparable ultrasound image volumes is acquired according to the size of the breast for facilitating year-over-year comparisons and/or a variety of other useful purposes.

DETAILED DESCRIPTION

Figure 1:
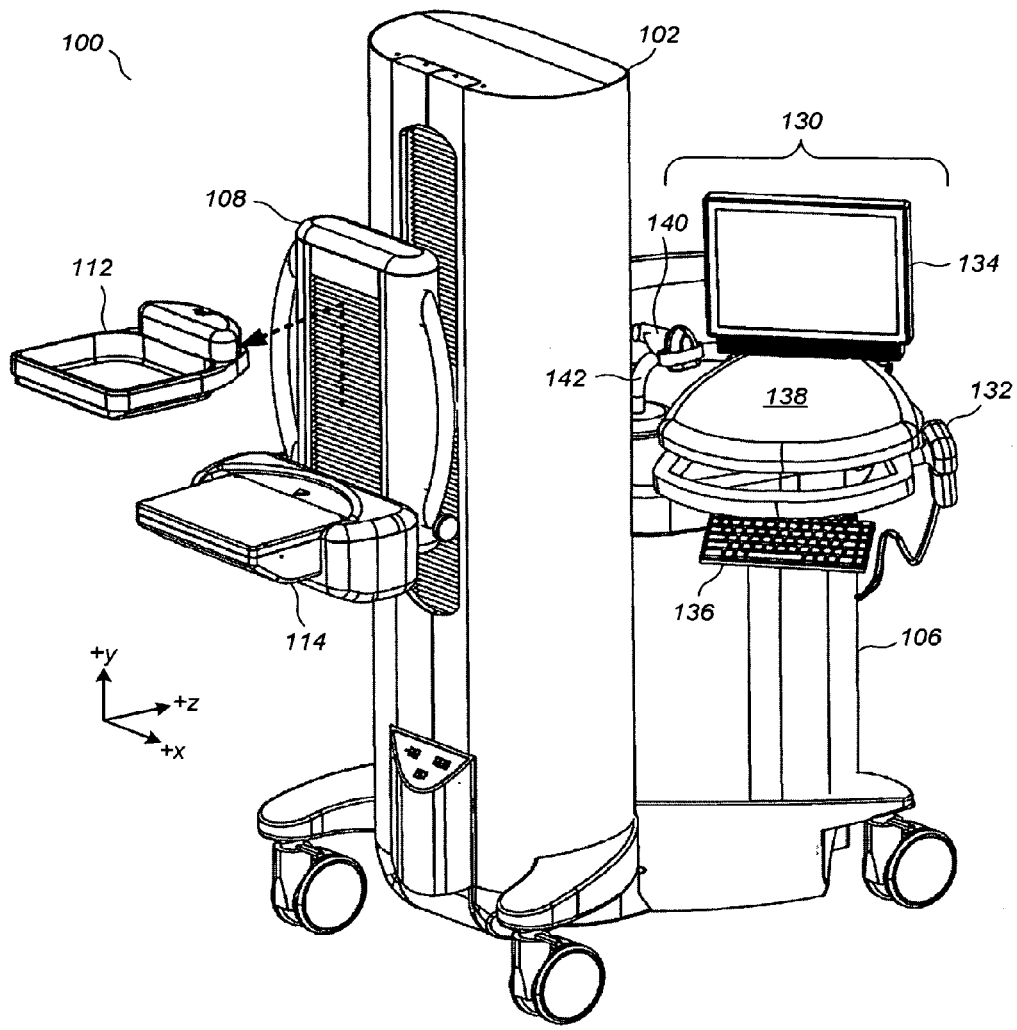
FIG. 1 illustrates a perspective view of a scanning apparatus according to a preferred embodiment.

FIG. 1 illustrates a perspective view of a full-field breast ultrasound (FFBU) scanning unit 100 according to a preferred embodiment. FFBU scanning unit 100 is similar in many respects to that described in WO 2004/030523A2, supra, except that an upper compressive member 112 has been configured, using methods known in the art, to be field-removable by the end user. FIG. 1 shows the upper compressive member 112 in a removed state.

FFBU scanning unit 100 comprises a rigid housing 102 that is made substantially non-movable when the product is in use by locking the caster wheels. Near location 106, FFBU scanning unit 100 comprises a fully functional ultrasound engine for driving an ultrasound transducer and generating volumetric breast ultrasound data therefrom. The volumetric scan data can be transferred to another computer system for further processing using any of a variety of data transfer methods known in the art. A general purpose computer, which can be implemented on the same computer as the ultrasound engine, is also provided for general user interfacing and system control. The general purpose computer can be a self-contained stand-alone unit, or can be remotely controlled, configured, and/or monitored by a remote station connected across a network.

FFBU scanning unit 100 movably supports a gantry 108 that in turn supports a breast compression and scanning assembly that includes a field-removable compression assembly 112, and a scanning assembly 114. The gantry 108 is vertically movable for accommodating patients of different heights, including patients in wheelchairs. The gantry 108 is rotatable from −180 degrees to +180 degrees around the z-axis in FIG. 1, i.e. around an axis parallel to an anterior-posterior direction. This allows scanning from any angle. The gantry 108 can be rotated, automatically and/or manually, to any angle for allowing, for example, mediolateral oblique (MLO) scans of either breast, including purely medial-lateral (ML) scans at −90 degrees and +90 degrees. Methods similar to those described in WO 2004/030523A2, supra, are used to obtain scans if the breast is to be compressed along a CC, MLO, or other anti-coronal plane.

FFBU scanning unit 100 further comprises a "conventional" ultrasound user interface 130 as would accompany a stand-alone handheld ultrasound scanning unit. Accompanying a handheld probe 132 are a display monitor 134, a keyboard 136, and a panel 138 for housing the many known switches, buttons, trackball, etc. (not shown) as would accompany a conventional ultrasound system. During an FFBU scanning mode, the display monitor 134 provides for user input and real-time feedback during the scanning process. However, in a handheld mode, the ultrasound user interface 130 operates like a known, conventional handheld ultrasound unit.

FFBU unit 100 further comprises a manual bar code scanner 140 that is removably positioned in a holder 142. The bar code scanner 140 is used to identify the patient by scanning their barcode off their medical file, medical images, or other document used in the relevant HIS/RIS system. This saves the extra effort that would be required to manually identify the patient using the keyboard or other manual input.

Figure 2:
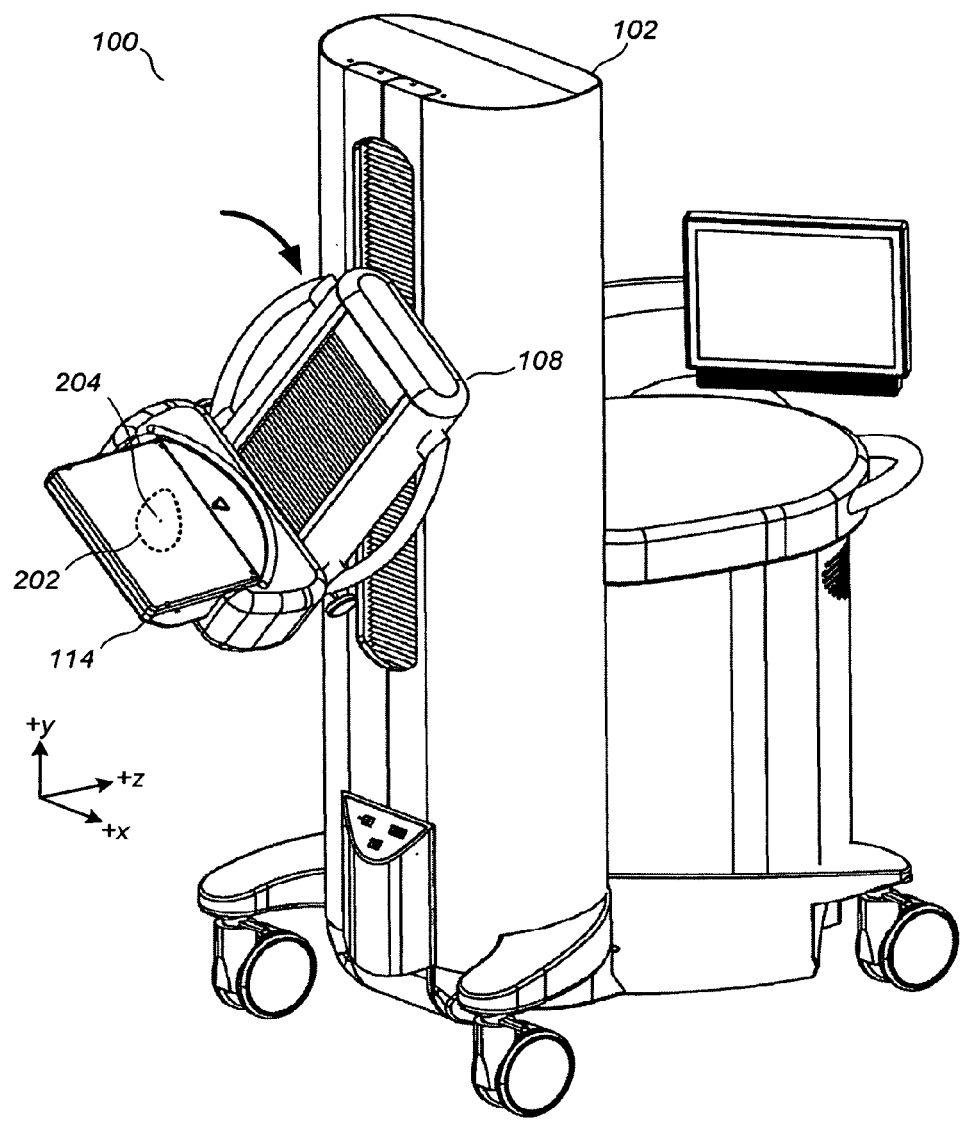
FIG. 2 illustrates a perspective view of a scanning apparatus according to a preferred embodiment.

FIG. 2 illustrates the FFBU scanning unit 100 as positioned for a head-on scan of a right breast of a patient. The gantry 108 is rotated to an angle of about 45 degrees, such that a patient can lean over onto the surface of the scanning assembly 114. The breast is chestwardly compressed in a firm yet comfortable way, as it is the patient's own body weight that is causing the compressive force. The dotted line 202 shows a locus of contact of the breast with the scanning surface, and a point 204 indicates where the nipple of the breast would be. For clarity of disclosure, the ultrasound user interface 130 is omitted in FIG. 2.

Figure 3:
FIG. 3 illustrates a perspective view of a patient receiving a head-on scan of a chestwardly-compressed breast according to a preferred embodiment.

FIG. 3 illustrates a perspective view of a patient receiving a head-on scan of a chestwardly-compressed breast according to a preferred embodiment. As indicated, the right arm of the patient can be comfortably placed over the upper edge of the scanning surface.

Figure 4:
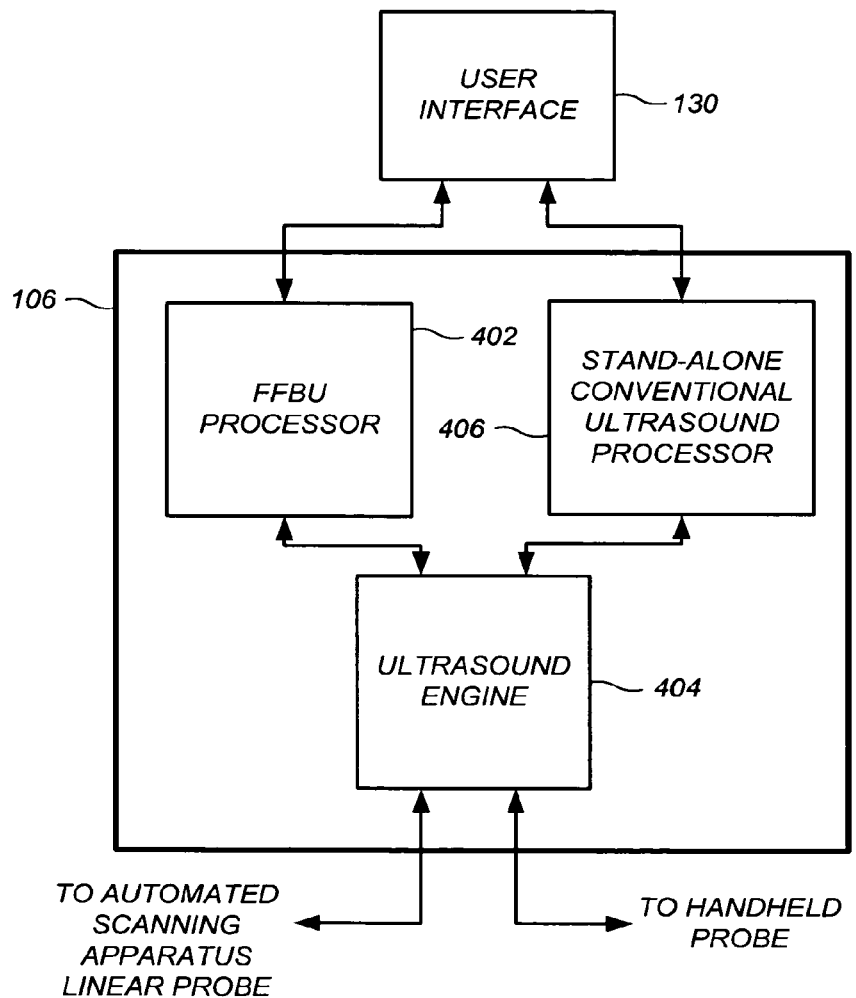
FIG. 4 illustrates a conceptual schematic view of processing components of the scanning apparatus of FIG. 2.

FIG. 4 illustrates a conceptual schematic view of processing components 106 of the scanning apparatus of FIGS. 1-2. An FFBU processor 402 controls the FFBU scanning functionality and the user interface 130 in an FFBU scanning mode, while an ultrasound engine 404 receives and processes the raw ultrasound data. A conventional ultrasound system front end processor 406 controls the user interface 130 in a conventional handheld scanning mode. Although drawn as separate components in FIG. 4, the processors 402, 404, and 406 may be integrated into a common processor running different software modules.

Figure 5:
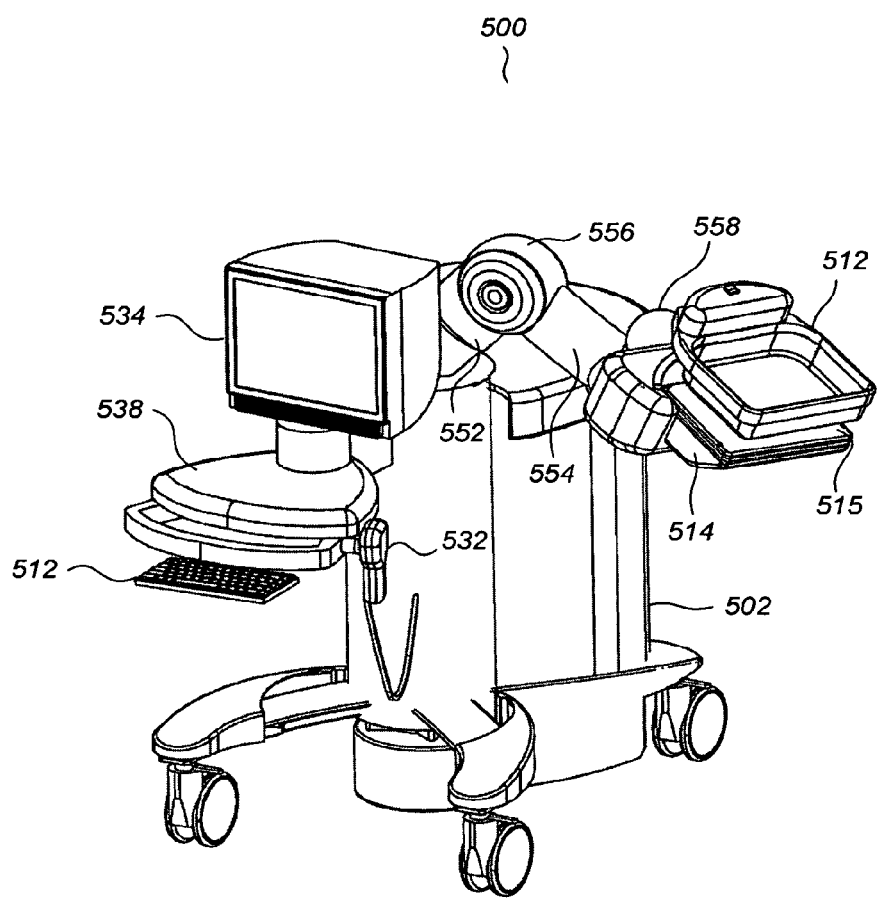
FIGS. 5-6 illustrate perspective views of a scanning apparatus according to a preferred embodiment.
Figure 6:
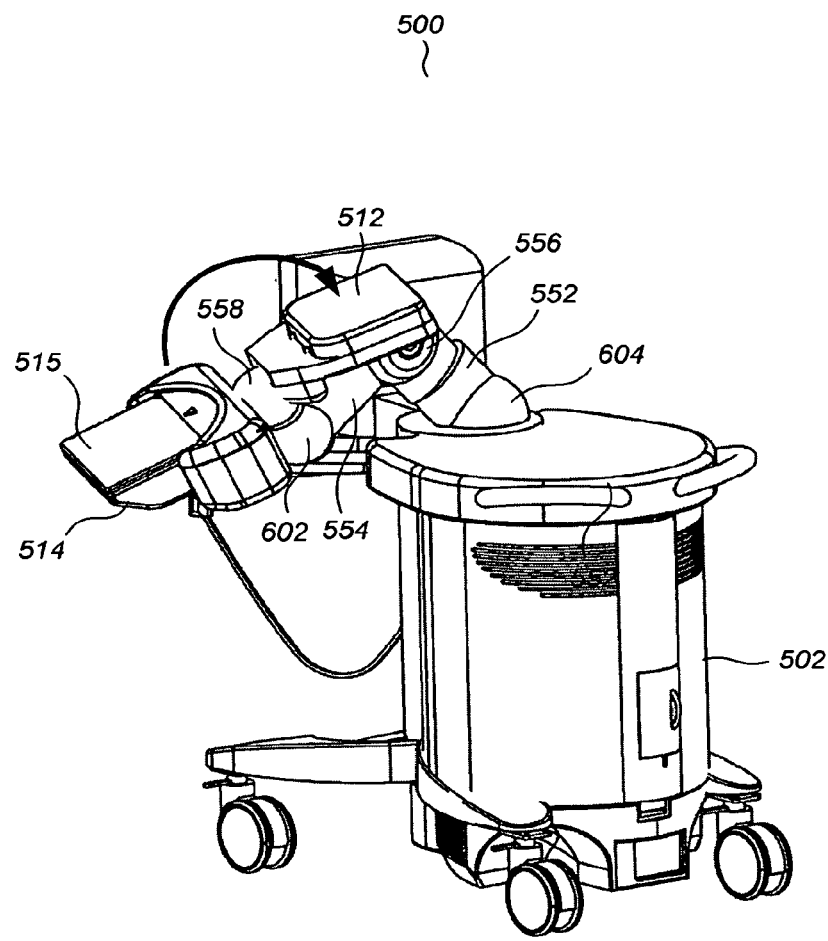

FIGS. 5-6 illustrates front and rear perspective views, respectively, of a multifunctional scanning unit 500 according to another preferred embodiment. The scanning unit 500 is similar to the scanning unit 100 of FIG. 1 in many respects, but has an upper compression assembly 512 that can be flipped out of the way instead of being removed from the unit to accommodate head-on breast scans.

Scanning unit 500 comprises a rigid housing 502 that is made substantially non-movable when the product is in use by locking the caster wheels. A "conventional" ultrasound user interface as would accompany a stand-alone handheld ultrasound scanning unit is provided. Accompanying a handheld probe 532 are a display monitor 534, a keyboard 536, and a panel 538 for housing the many known switches, buttons, trackball, etc. (not shown) as would accompany a conventional ultrasound system. During an FFBU scanning mode, the display monitor 534 provides for user input and real-time feedback during the scanning process. However, in a handheld mode, the ultrasound user interface operates like a known, conventional handheld ultrasound unit. Processing components are similar to those of the apparatus of FIGS. 1, 2, and 4.

Scanning unit 500 pivotably supports a support arm comprising a first rigid member 552 and a second rigid member 554 coupled by a hingeable joint 556. A turret-like arrangement 604 allows the support arm to be rotated at most angles around the device, and to be raised and lowered. The support arm in turn supports a breast compression and scanning assembly that includes a the compression assembly 512 and a scanning assembly 514. The scanning assembly 514 can be raised, lowered, tilted forward or backward, and tilted left or right (i.e., around an anterior-posterior axis) relative to the patient to any of a variety of locations most convenient for a given patient or class of patients. As indicated in FIGS. 5-6, the compression assembly 512 can, in a first configuration, be raised and lowered relative to the scanning assembly 514 for compressing the breast along the CC, MLO, or other substantially anti-coronal plane. In a second configuration, the compression assembly 512 can be tilted backward (see FIG. 6) to allow room for head-on scanning, and does not need to be removed altogether from the device. The scanning assembly 514 includes a surface 515 comprising a taut membrane comprising Mylar or similar material, and/or other materials as described in WO 2004/030523A2, supra.

In the preferred embodiment of FIGS. 5-6 there are (i) ball-joint-like mechanisms 558 and 602, (ii) hinge-like mechanism 556, and turret-like mechanism 604 used to achieve the above functionalities. However, the scope of the preferred embodiments is not limited to these particular types of mechanical implementations. Rather, any of a variety of different mechanisms can be used to achieve the above-described capabilities without departing from the scope of the preferred embodiments.

Figure 7:
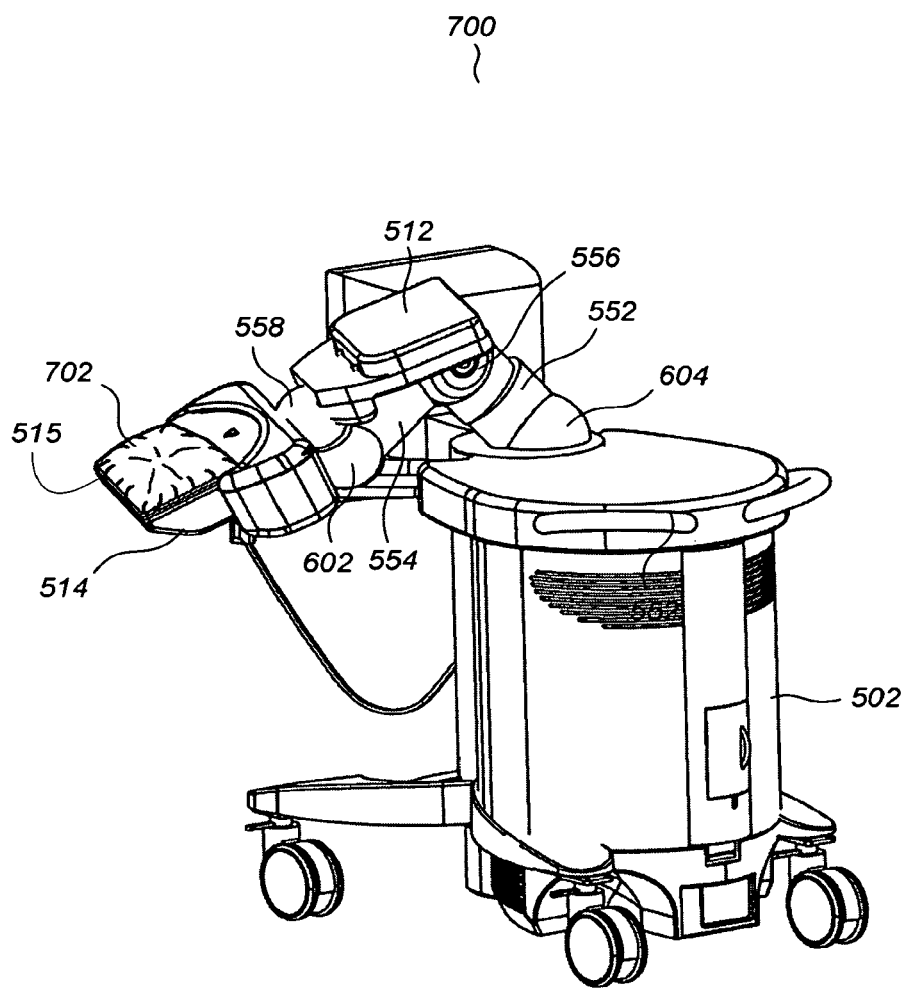
FIG. 7 illustrates a perspective view of a scanning apparatus according to a preferred embodiment.

FIG. 7 illustrates a rear perspective views of a scanning unit 700 similar to that of FIGS. 5-6, but provided with a gel pad 702 integrated into the scanning assembly 514 atop the surface 515. The gel pad 702 promotes improved patient comfort while also promoting better acoustic coupling with a chestwardly-compressed breast for head-on scans.

Figure 8:
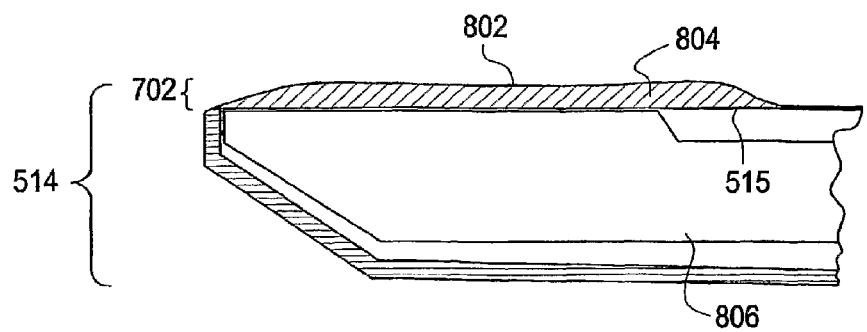
FIG. 8 illustrates a side view of an integral gel pad formed on a compressive member of a scanning assembly according to a preferred embodiment.
Figure 9:
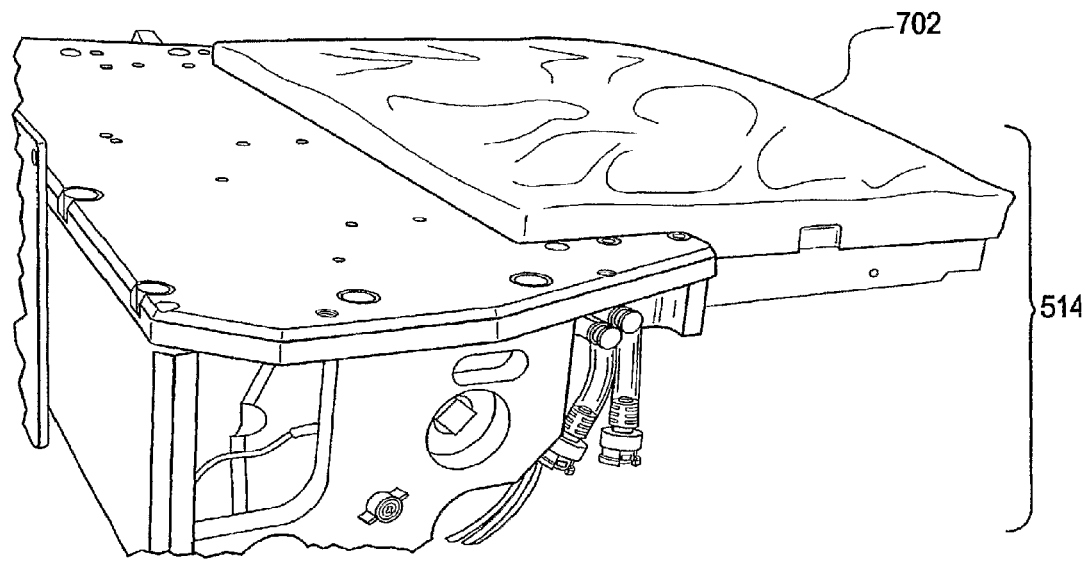
FIG. 9 illustrates a perspective view of the integral gel pad of FIG. 8.

FIG. 8 illustrates a side view of the gel pad 702 as integrated into the scanning assembly 514. Gel pad 702 is formed from a layer 802 of silicone rubber, preferably between 0.5 mm and 1.0 mm thick that is sealably placed around the periphery of the surface 515 of the scanning assembly. The layer 802 and surface 515 form a closed slab-like cavity that is filled with a relatively viscous, acoustically conductive gel 804. The gel 804 is readily displaced around the skinline of the breast as the breast is compressed inward toward the surface 515, promoting both patient comfort and acoustic coupling. The gel 804 can comprise Dow Corning 7-9600 Soft Filling Elastomer, Dow Corning Q3-6575 Dielectric Gel, or other materials having similar physical and acoustic characteristics. By way of nonlimiting example, the gel pad 702 can be approximately ½" (1.27 cm) thick. Also shown in FIG. 8 is a side view of the linear ultrasound probe 806, which is swept in a direction corresponding to in-and-out of the paper in FIG. 8. FIG. 9 illustrates a perspective view of the integral gel pad of FIG. 8.

Figure 10:
FIG. 10 illustrates a perspective view of a patient receiving a head-on scan of a chestwardly-compressed breast according to a preferred embodiment in which the patient is standing upright.
Figure 11:
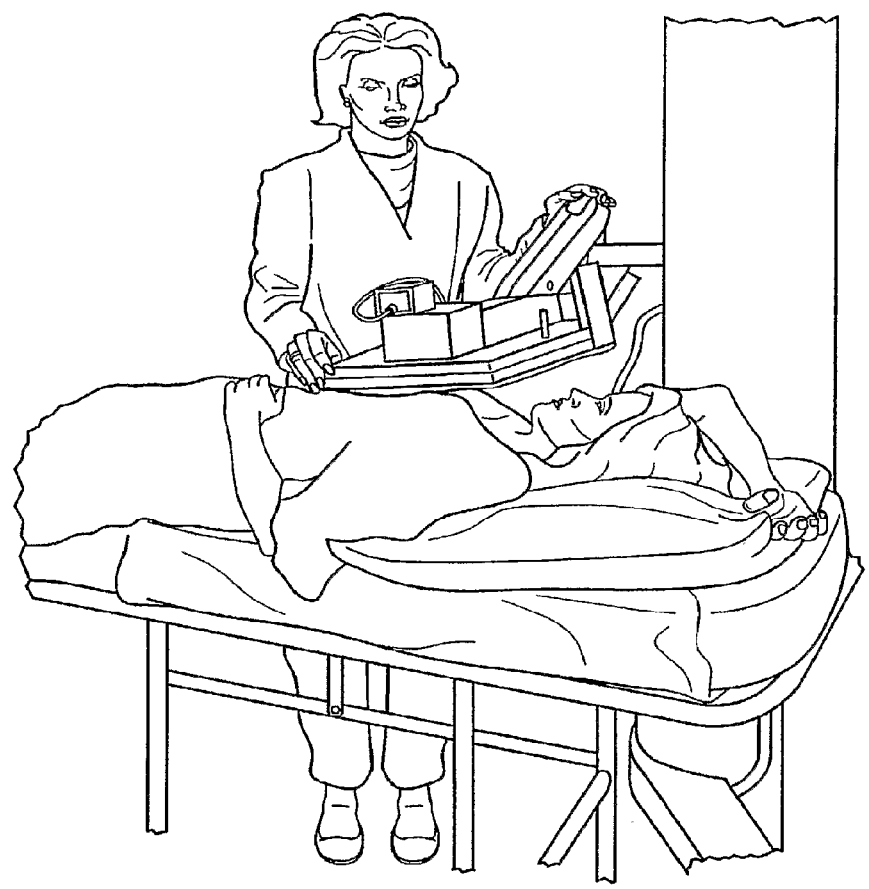
FIG. 11 illustrates a perspective view of a patient receiving a head-on scan of a chestwardly-compressed breast according to a preferred embodiment in which the patient is fully supine.

FIG. 10 illustrates a perspective view of a patient receiving a head-on scan of a chestwardly-compressed breast according to a preferred embodiment, in which the patient is standing upright. FIG. 11 illustrates a perspective view of a patient receiving a head-on scan of a chestwardly-compressed breast according to a preferred embodiment in which the patient is fully supine. The described FFBU scanning apparatus is adapted and configured to allow for head-on breast scanning in a variety of positions including prone, standing while leaning forward, standing upright, partially supine, and fully supine positions.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, while described supra in terms of having a membranous compression/scanning surface, in other preferred embodiments the compression/scanning surface can be a thin, rigid material such as polycarbonate plastic, or other materials that are described in U.S. Pat. No. 6,574,499, which is incorporated by reference herein. By way of further example, in another preferred embodiment, the acoustic coupling between the scanning probe and the membrane can be achieved by means other than an irrigation system. For example, the closed chamber formed by the scanning assembly housing and the membrane can be completely filled with an acoustic couplant such as oil. Any or all of the above components that support the scanning assembly (gantry, arms, joints, etc.) can be motorized using methods known in the art for easy operation. Predetermined position settings for each patient, or type of patient, can be used to place the device in the proper physical configuration automatically.

By way of further example, rigid lateral preforms can be provided for placement on the first compressive member to facilitate head-on scanning. In general, the rigid lateral preforms would have an appearance of a shallow cylinder, similar perhaps to the shape of an egg ring or a pancake ring. The breast would be entered into the rigid lateral preform and fill out the preform, with most of the breast surface being flattened against the Mylar. A thin gel pad similar to that of FIG. 7, except thinner, can optionally be provided atop the Mylar inside of the rigid lateral preform to fill in small corners that might otherwise exist at the preform-Mylar interface. Therefore, reference to the details of the preferred embodiments are not intended to limit their scope, which is limited only by the scope of the claims set forth below.

Figure 12:
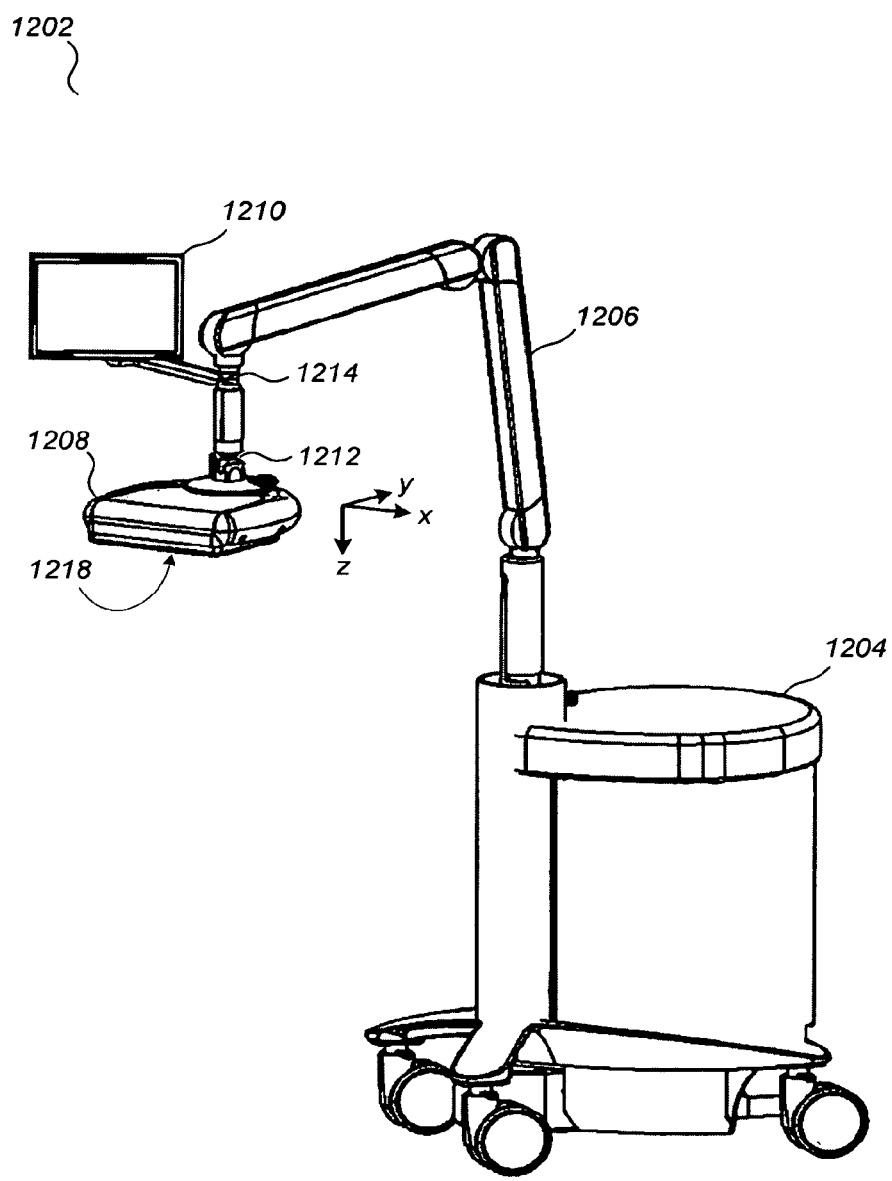
FIG. 12 illustrates a perspective view of a scanning apparatus according to a preferred embodiment.

FIG. 12 illustrates a perspective view of a full-field breast ultrasound (FFBU) scanning apparatus 1202 according to a preferred embodiment, comprising a frame 1204 that may contain an ultrasound processor, a movable support arm 1206, a compression/scanning assembly 1208 connected to the support arm 1206 via a ball-and-socket connector 1212, and a monitor 1210 connected to the support arm 1206 at a joint 1214. Preferably, the support arm 1206 is configured and adapted such that the compression/scanning assembly 1208 is either (i) neutrally buoyant in space, or (ii) has a light net downward weight (e.g., 2-3 pounds) for breast compression, while allowing for easy user manipulation. According to a preferred embodiment, the compression/scanning assembly 1208 comprises an at least partially conformable membrane 1218 in a substantially taut state, the membrane 1218 having a bottom surface contacting the breast while a transducer is swept across a top surface thereof to scan the breast. Optionally, the support arm 1206 may comprise potentiometers (not shown) to allow position and orientation sensing for the compression/scanning assembly 1208, or other types of position and orientation sensing (e.g., gyroscopic, magnetic, optical) can be used. By way of example and not by way of limitation, a miniBIRD® 3D position sensor from Ascension Technologies can be used to determine the position and orientation of the compression/scanning assembly 1208 on a per-frame basis.

Within frame 1204 may be provided a fully functional ultrasound engine for driving an ultrasound transducer and generating volumetric breast ultrasound data from the scans in conjunction with the associated position and orientation information. The volumetric scan data can be transferred to another computer system for further processing using any of a variety of data transfer methods known in the art. A general purpose computer, which can be implemented on the same computer as the ultrasound engine, is also provided for general user interfacing and system control. The general purpose computer can be a self-contained stand-alone unit, or can be remotely controlled, configured, and/or monitored by a remote station connected across a network.

The compression/scanning assembly 1208 is preferably a substantially self-contained, pod-like module that can be grasped by the hands of a user and manipulated to compress the breast in a generally chestward direction. By generally chestward, it is meant that membrane 1218 of the compression/scanning assembly 1208 urges the breast surface toward the chest wall of the patient while the membrane is an angle of 45 degrees or less from a coronal plane. It has been found that, generally speaking, the breasts of supine or reclining women can have many different tendencies depending on the anatomy of the woman. For example, for first fully supine woman the breast may droop upward toward the shoulder, while for a second fully supine woman the breast may droop downward toward the abdomen or inward toward the sternum. For these breasts it may be desirable to tilt the scanning surface somewhat relative to the coronal plane, obtaining a scan of the breast while pushing the breast at least partially sideways toward the theoretical center of the breast and while also pushing it inward toward the chest wall.

Notably, the scope of the preferred embodiments is not limited to the above-referenced angles relative to the coronal plane. In other preferred embodiments any of a variety of different angles and orientations may be used, depending on the circumstances. Thus, in another example, there may be an older, large-breasted woman with highly pendulous breast tissue. In that case, it may be desirable to have the woman stand upright, and the compression/scanning assembly 1208 might be positioned underneath the breast, serving as a sort of platform or table for the breast to rest on. In this case, the membrane 1218 would be almost at a 90 degree angle relative to the coronal plane. Depending on the results, the platform could be tilted a little more in the chestward direction to better image the chest wall, e.g., at a 60-75 degree angle relative to the coronal plane. In distinction, for smaller-breasted women, a direct head-on angle of zero degrees relative to the coronal plane will be more appropriate in most cases. The ability to perform scans at this variety of angles is facilitated by providing the end of the support arm 1206 with all three translational degrees of freedom (e.g., x, y, and z), and providing the compression/scanning assembly 1208 with all three rotational degrees of freedom (e.g., pitch, roll, and yaw) relative to the end of the support arm 1206 via the ball-and-socket connector 1212. The monitor 1210 is conveniently and movably positioned near the end of the support arm 1206 for easy viewing by the user in any of a variety of positions.

Figure 13:
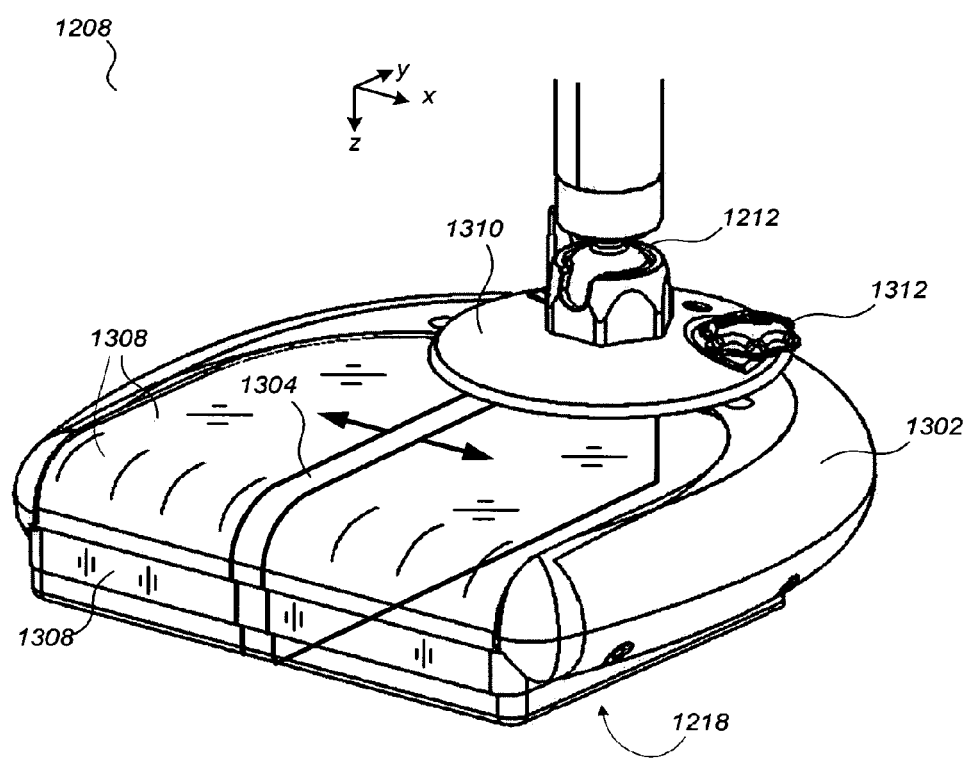
FIG. 13 illustrates a perspective view of a compression/scanning assembly of the scanning apparatus of FIG. 12.

FIG. 13 illustrates a perspective view of the compression/scanning assembly 108, which comprises a housing 1302 and a linear array transducer 1304. In one preferred embodiment, the transducer 1304 comprises 768 piezoelectric transducer elements. Transducer types other than linear array transducers, such as 1.25D, 1.5D or 2D transducers are also within the scope of the preferred embodiments. The housing 1302 forms an opening on its underside, across which is positioned the membrane 1218. In one embodiment, the acoustic coupling at the interface between the transducer 204 and the membrane 1218 is facilitated by dynamic or static wetting with water or other low viscosity coupling agent as described, for example, in the commonly assigned WO 2004/030523A2, supra. In another preferred embodiment, a silicone oil can be used to facilitate the acoustic coupling. In one preferred embodiment, the membrane 1218 comprises a polyester film sheet. Examples can include 2 mil-thick Mylar® or Melinex®, although a variety of other suitable materials are within the scope of the preferred embodiments.

According to a preferred embodiment, in addition to the membrane 1218 comprising an optically transparent material, the housing 1302 also comprises an optically transparent portion 1308 in areas that would otherwise impede a view of the compressed breast surface. The optically transparent portion 1308 can comprise a substantially transparent acrylic or polycarbonate plastic, while the outer non-transparent portions of the housing 1302 can comprise any of a variety of thermoform plastics. The transparency of the housing 1302 in these areas can make positioning and monitoring of the scanning process much easier, and accordingly improve the quality of the acquired scans. Because normal usage can result in scratches or other degradation of the membrane 1218 over time, the membrane 1218 is preferably designed to be field-replaceable, such as by using pop-on and pop-off style framing in conjunction with the housing 1302, or by using screw-type fasteners or a quick-release lever.

Along a plate 1310 is a potentiometer knob 1312 that is manually rotated by the user to align a marker thereon with a head-to-toe direction of the patient, thereby providing information to the ultrasound system to orient the scan data. In other preferred embodiments, known anatomical structures visible in the ultrasound images can be used to automatically orient the scans. By way of example, the patient's the rib cage can be segmented from the resulting ultrasound data in order to facilitate automatic orientation of the images.

It is to be appreciated that the scope of the preferred embodiments is not limited to linear array probes performing linear-sweep scans across the surface of the membrane 1218. In other preferred embodiments, any of a variety of scanning motions (e.g., multiple linear sweeps, rotations, targeted scans of predetermined or dynamically determined sub-volumes of the breast, combinations of the above, etc) can be used. In still other preferred embodiments, the scanning surfaces are curved rather than flat, or partially curved along part(s) of the transducer array.

Figure 14:
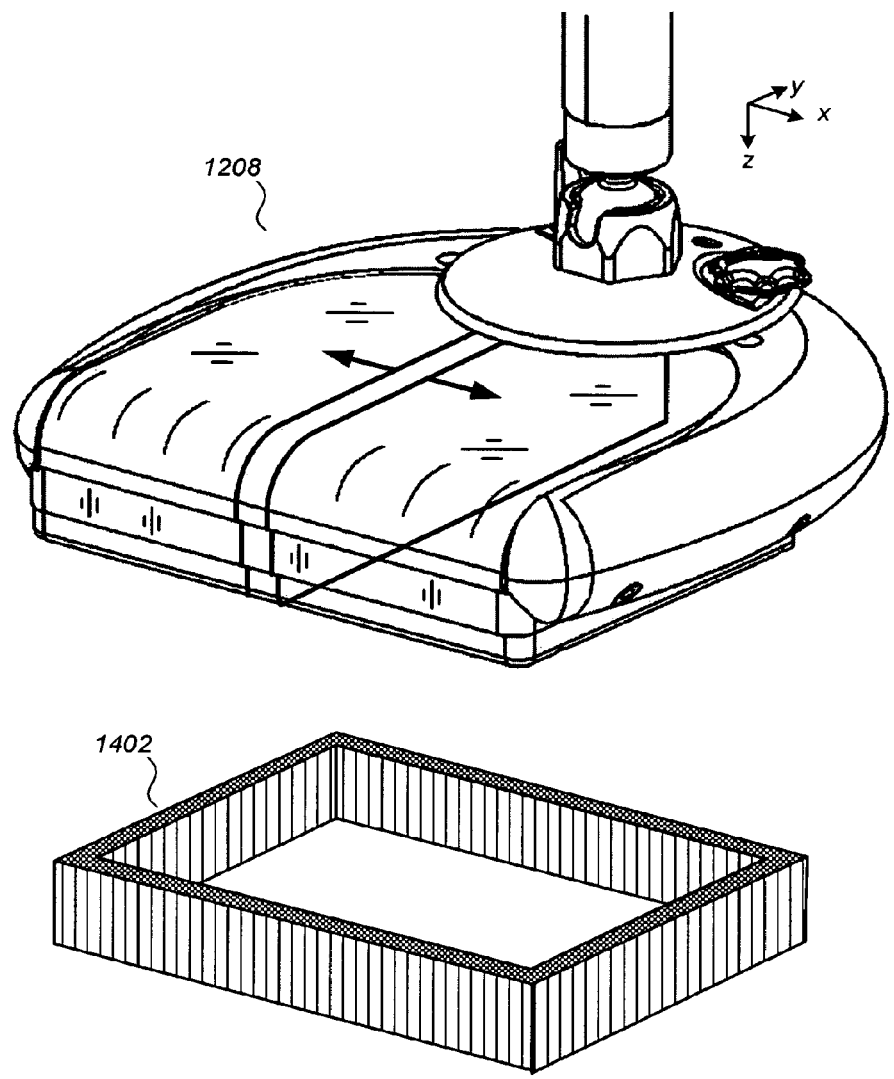
FIG. 14 illustrates a perspective view of the compression/scanning assembly of FIG. 13 and a lateral support element according to a preferred embodiment.

FIG. 14 illustrates a perspective view of the compression/scanning assembly 1208 with an attachable lateral support element 1402 according to a preferred embodiment. The lateral support element 1402 provides for gentle lateral confinement of the breast during the scans. In one preferred embodiment, the lateral support element 1402 comprises an at least partially pliable material such as a rubberized sponge material. The lateral support element 1402 is particularly useful for larger, pendulous breasts that might otherwise migrate over toward the side, or upward toward the shoulder, of a supine patient. In other preferred embodiments, the lateral support element 1402 may instead be provided as a stand-alone element not connected to the compression/scanning assembly 1208. In these preferred embodiments, the lateral support element 1402 is laterally positioned around the breast before the compression/scanning assembly 1208 is lowered thereon. Any of a variety of pre-formed or user-conformable materials capable of laterally confining the breast are within the scope of the preferred embodiments.

Figure 15:
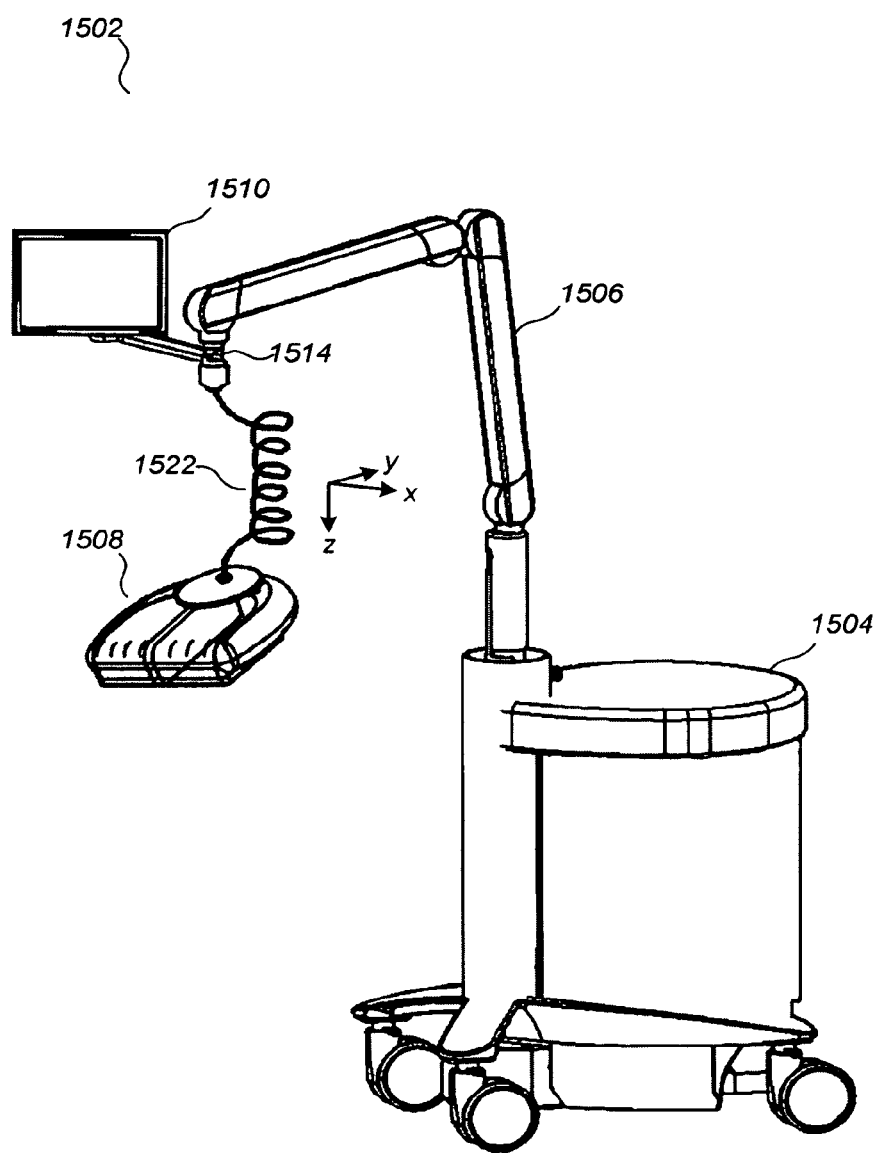
FIG. 15 illustrates a perspective view of a scanning apparatus according to a preferred embodiment.

FIG. 15 illustrates a perspective view of a scanning apparatus 1502 according to a preferred embodiment, comprising a frame 1504, a support arm 1506, a compression/scanning assembly 1508, and a monitor 1510 connected to the support arm 1506 at a joint 1514. The compression/scanning assembly 1508 is mechanically separated from the support arm 1506, being fully supported and manipulated by the user's hands. However, the compression/scanning assembly 1508 is electrically coupled to an ultrasound processor through a cable extending from the support arm 1506, the cable also providing backup support by suspending the compression/scanning assembly 1508 above the floor in case it is accidentally dropped or otherwise released by the user. Position sensing is optionally provided using gyroscopic means, optical means, magnetic means, etc. (not shown).

In other preferred embodiments, the compression/scanning assembly 1508 can completely stand alone, with no physical cables or mechanical connection to the remainder of the overall apparatus. In these embodiments, wireless digital communications or other electromagnetic radiation-based communications can be used to transfer the acquired scans to an ultrasound processor. In still other embodiments, battery power can be used such that not even a power cord is required, making the compression/scanning assembly truly portable.

Figure 16:
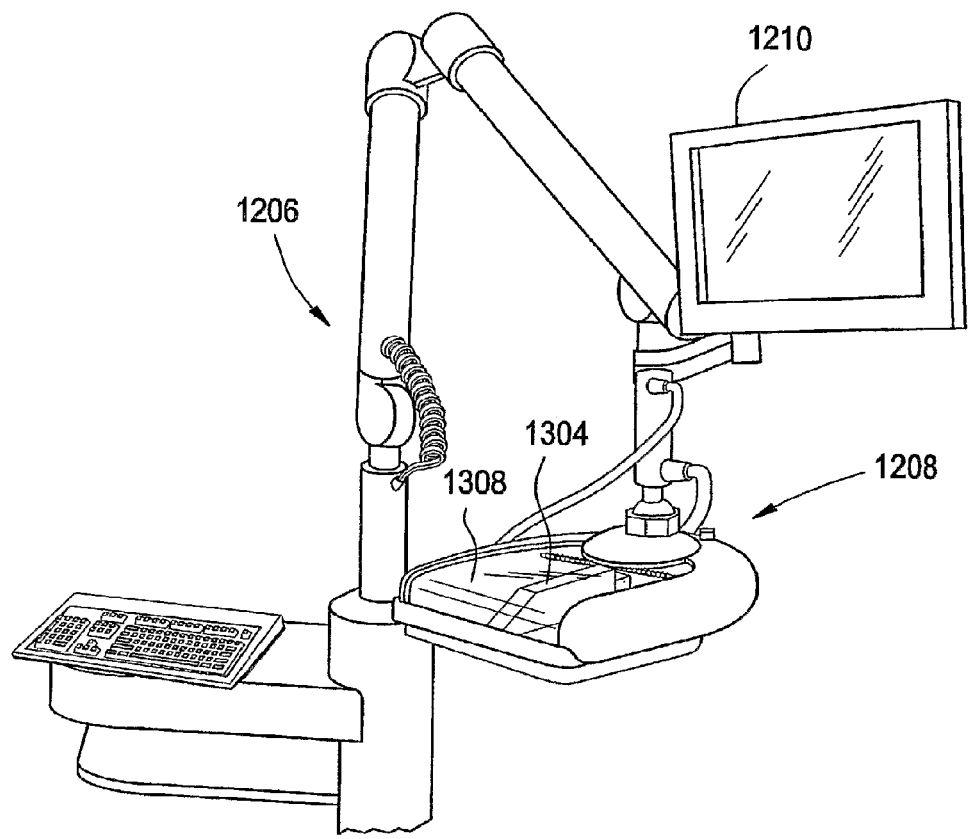
FIG. 16 illustrates a scanning apparatus according to a preferred embodiment.
Figure 17:
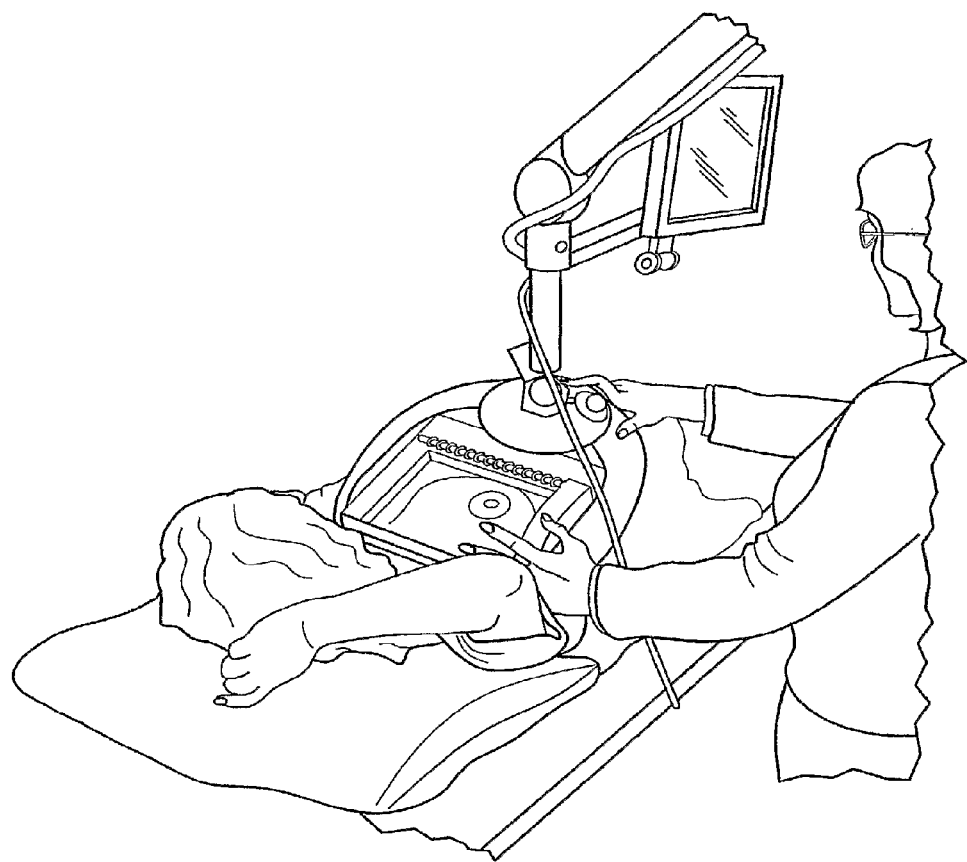
FIGS. 17-21 illustrate the scanning apparatus of FIG. 16 under control of a user while scanning the breasts of a patient according to a preferred embodiment.
Figure 18:
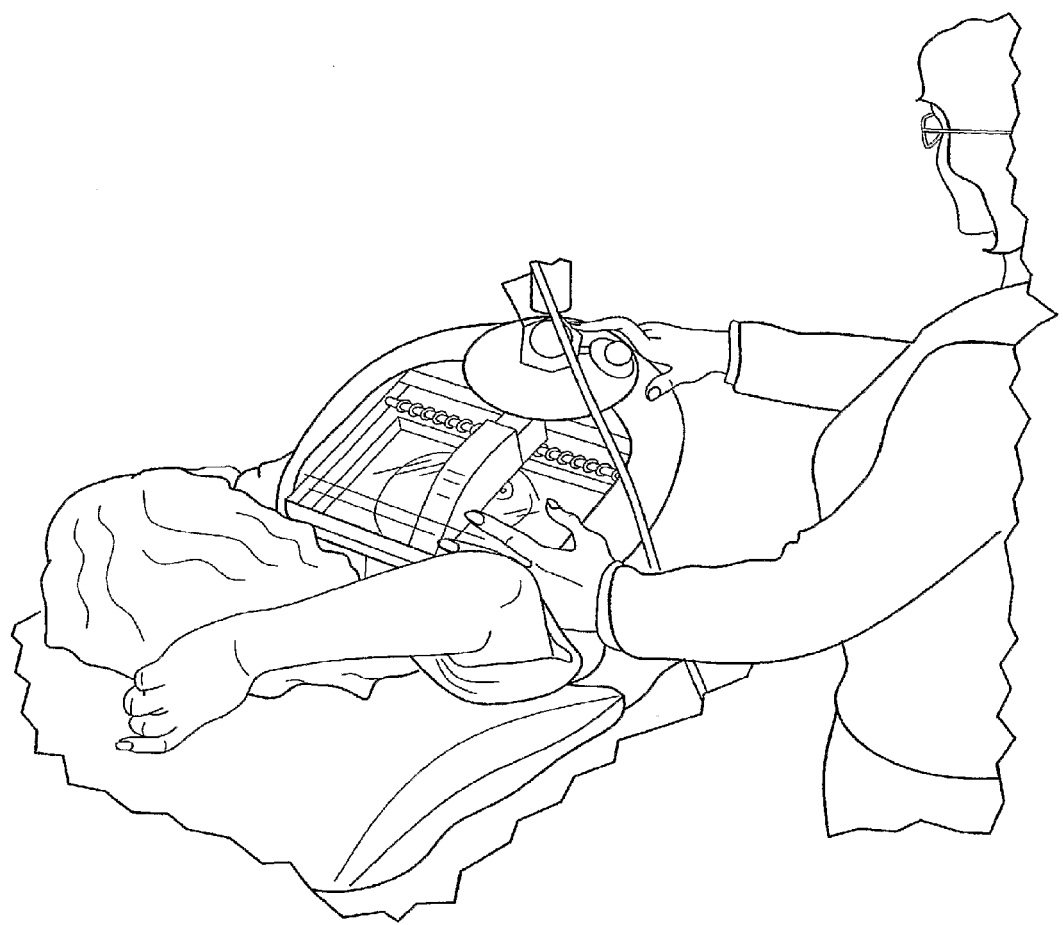
Figure 19:
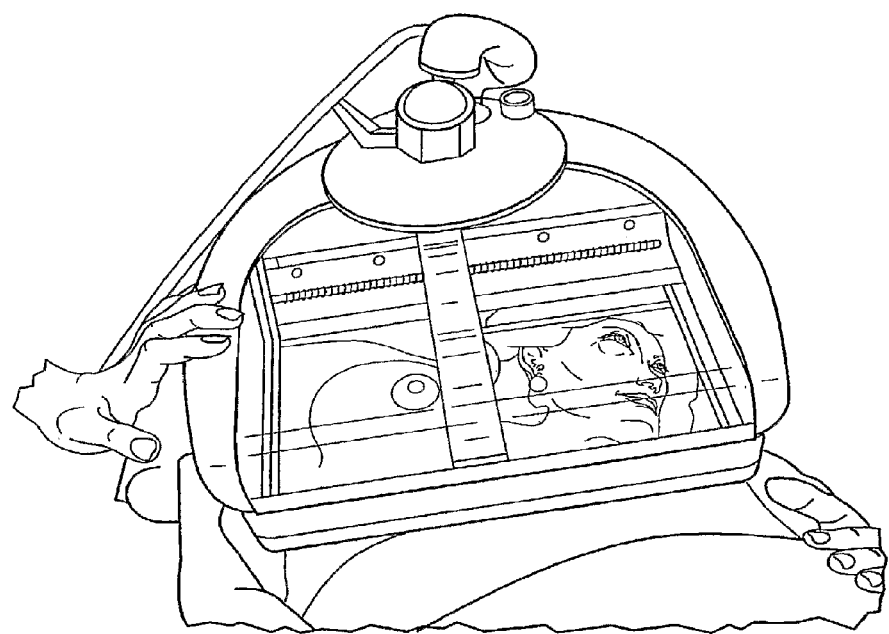
Figure 20:
Figure 21:

FIG. 16 illustrates a perspective view of a scanning apparatus similar to that of FIG. 12. FIGS. 17-21 illustrate the scanning apparatus of FIG. 16 under control of a user while scanning the breasts of a patient, illustrating just some of the many different scanning angles and orientations that are facilitated.

In addition to being easy to manipulate, the scanning apparatus further promotes patient comfort and reliable scanning because the patient can comfortably breathe during the procedure without confounding the scanning results, because the compression/scanning assembly rises up and down (or in and out) with the patient's chest. Further position and orientation sensors can optionally be placed on the patient's chest to detect relative motion between the compression/scanning assembly and the patient, where desired. Measurement of respiratory movement can thereby be achieved, and used to during formation of ultrasound volumes from the planar scans by compensating for respiratory movement.

Another important quality in a breast scanning system is its amenability to at least some degree of clinical systemization and/or standardization. According to a preferred embodiment, provided in conjunction with a pod-like, hand-manipulable scanner such as the compression/scanning assemblies 1208 and 1508, supra, are methods facilitating, among other useful objectives, (i) the ability to have the same breast scanned the same way in different years to provide meaningful year-over-year comparisons, and (ii) the ability to more easily compare of tissue structures in different patients having similarly-formed breasts. According to a preferred embodiment, a method for ultrasonically scanning a breast is provided, comprising stationarily pressing (i.e., holding substantially motionless while pressing) a substantially planar compressive surface of a hand-manipulable ultrasound scanning unit against the breast in a generally chestward direction, the hand-manipulable ultrasound scanning unit including an ultrasound transducer that is swept across the planar compressive surface to scan the breast therethrough while the compressive surface is stationarily pressed against the breast.

Figure 22:
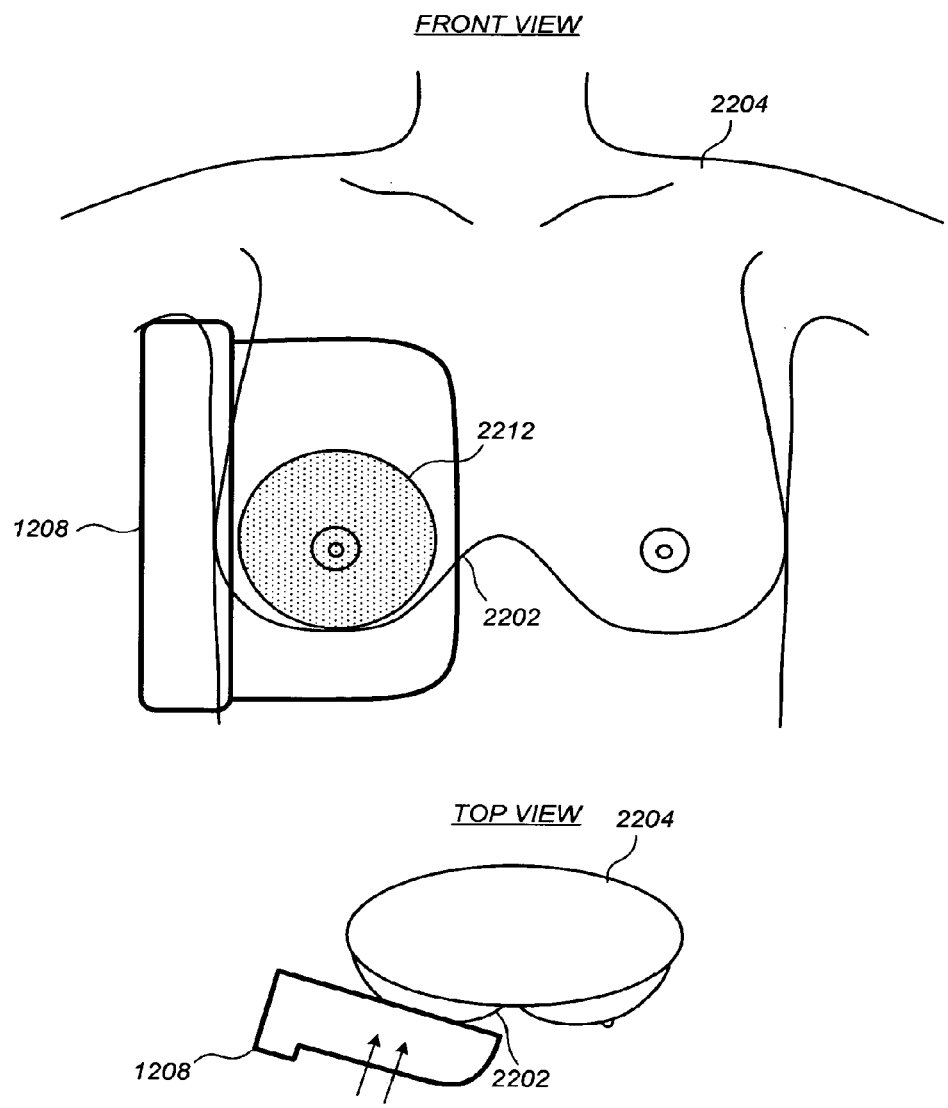
FIG. 22 illustrates a diagram of head-on breast ultrasound scanning according to a preferred embodiment.

FIG. 22 illustrates a diagram of head-on breast ultrasound scanning according to a preferred embodiment, in which a breast 2202 of a patient 2204 is scanned using the compression/scanning assembly 1208 of FIG. 12, supra. Alternatively, the compression/scanning assembly 1508 of FIG. 15 can be used, or more generally any similar assembly having a substantially planar scanning surface that is rigid or semi-rigid as compared to the general softness of a breast. For some clinical settings and/or patient groups, it is often considered sufficient to use a single head-on scan to volumetrically image a dense-disk region 2212 of the breast, the compressive surface being substantially parallel to the coronal plane and chestwardly pressed against the breast.

In other clinical settings and/or for other patient groups, it is often desired to more thoroughly scan the breast by obtaining ancillary compressive scans at one or more off-coronal angles. However, according to a preferred embodiment, at least some degree of systemization and/or standardization is maintained by using lateral frontal, medial frontal, inferior frontal, and/or superior frontal compression and scanning orientations as described herein. In one preferred embodiment, the image volumes acquired from the ancillary compressive scans are used to supplement the image volume acquired from the head-on scan. In another embodiment, the single head-on scans are omitted and only the image volumes acquired from the ancillary compressive scans are used.

Figure 23:
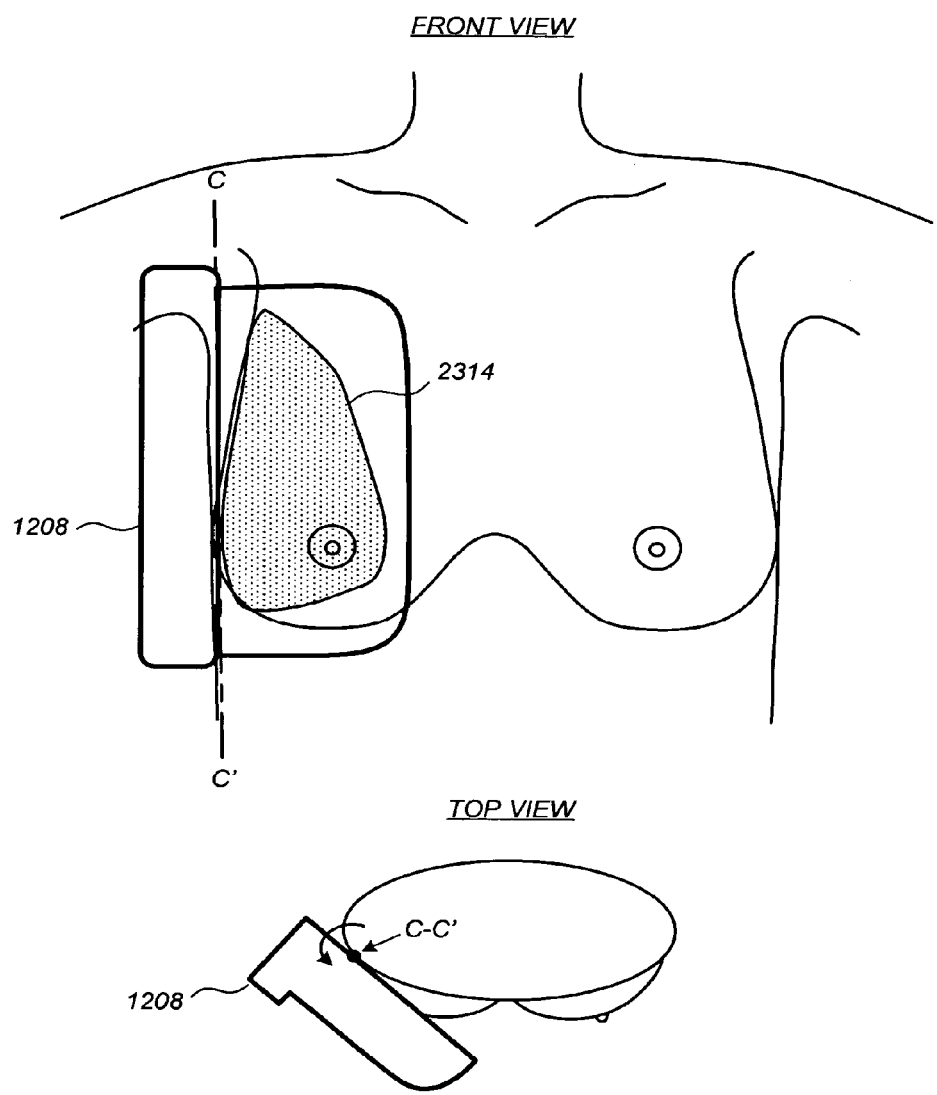
FIG. 23 illustrates a diagram of lateral frontal breast ultrasound scanning according to a preferred embodiment.

FIG. 23 illustrates a diagram of lateral frontal breast ultrasound scanning according to a preferred embodiment, in which the compression/scanning assembly 1208 is manipulated to image a lateral frontal region 2314. Preferably, in a positioning process preceding the probe sweep, one side of the compressive surface is pinned adjacent to the outer edge of the breast (near the line C-C' in FIG. 23) and then the compressive surface is "rolled" toward the medial side of the breast, until a position is reached in which the compressive surface would lift away from C-C' if the rolling continued. This has been found to allow capturing of a relatively large lateral frontal region 2314 that usually includes the nipple, while also minimizing small air pockets, bubbles, etc. that can degrade image quality.

Figure 24:
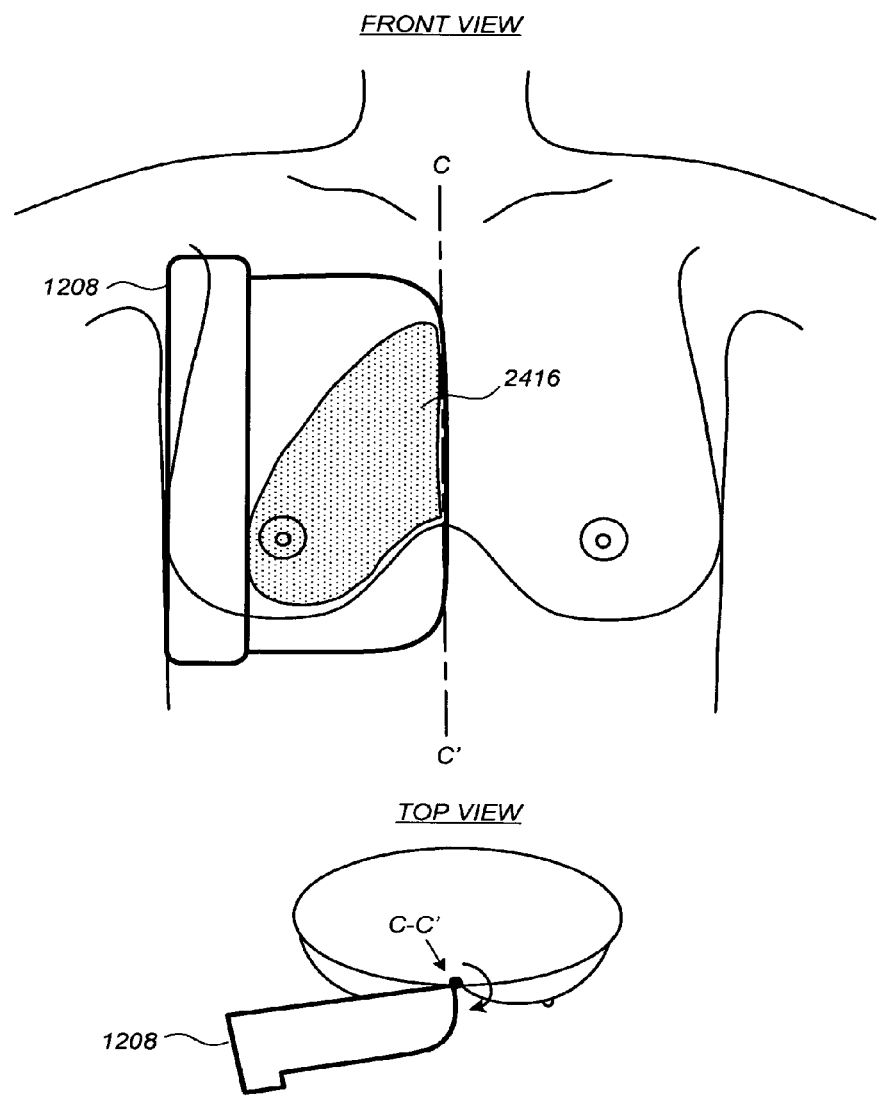
FIG. 24 illustrates a diagram of medial frontal breast ultrasound scanning according to a preferred embodiment.

FIG. 24 illustrates a diagram of medial frontal breast ultrasound scanning according to a preferred embodiment, in which the compression/scanning assembly 1208 is manipulated to image a medial frontal region 2416. In a manner analogous to the lateral frontal scan, one side of the compressive surface is preferably pinned adjacent to the medial edge of the breast (near the line C-C' in FIG. 24) and then the compressive surface is "rolled" toward the outer side of the breast, until a position is reached in which the compressive surface would lift away from C-C' if the rolling continued.

Figure 25:
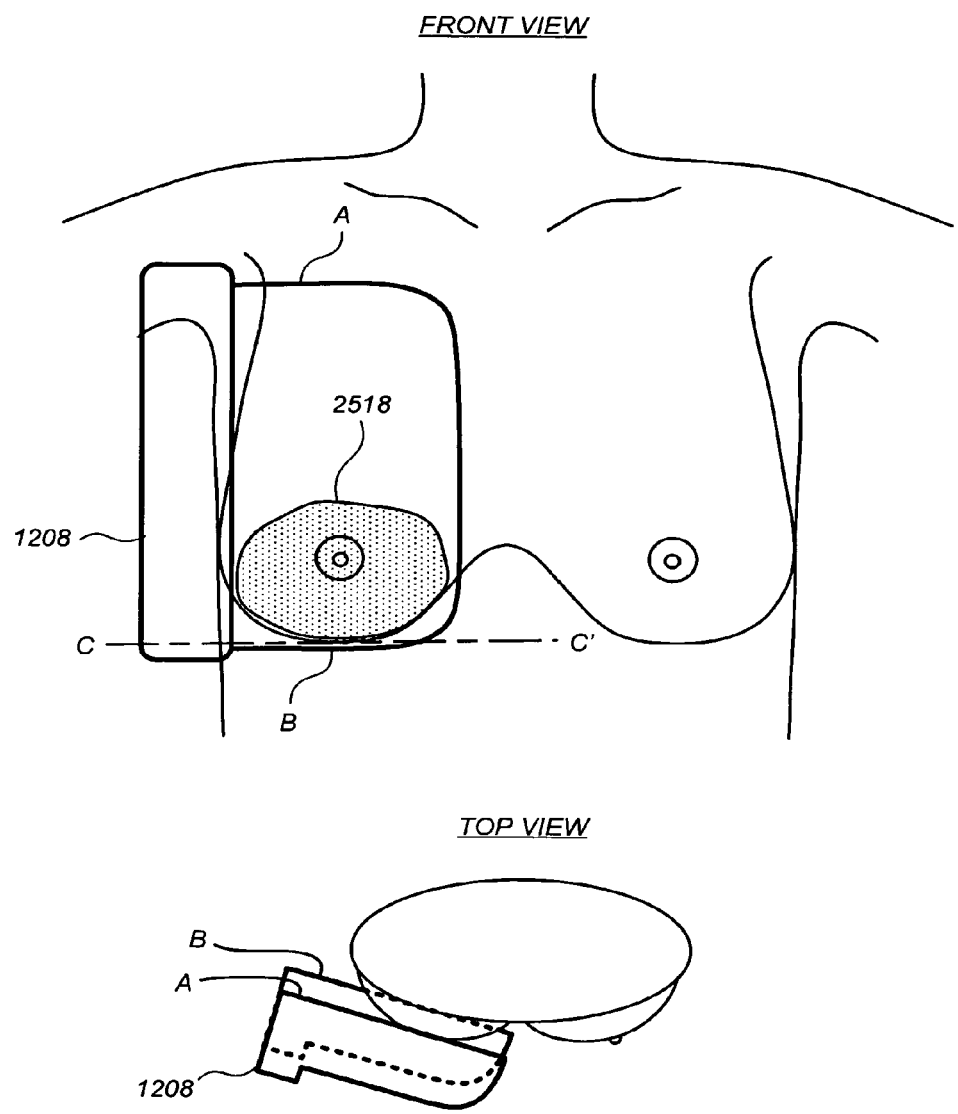
FIG. 25 illustrates a diagram of inferior frontal breast ultrasound scanning according to a preferred embodiment.
Figure 26:
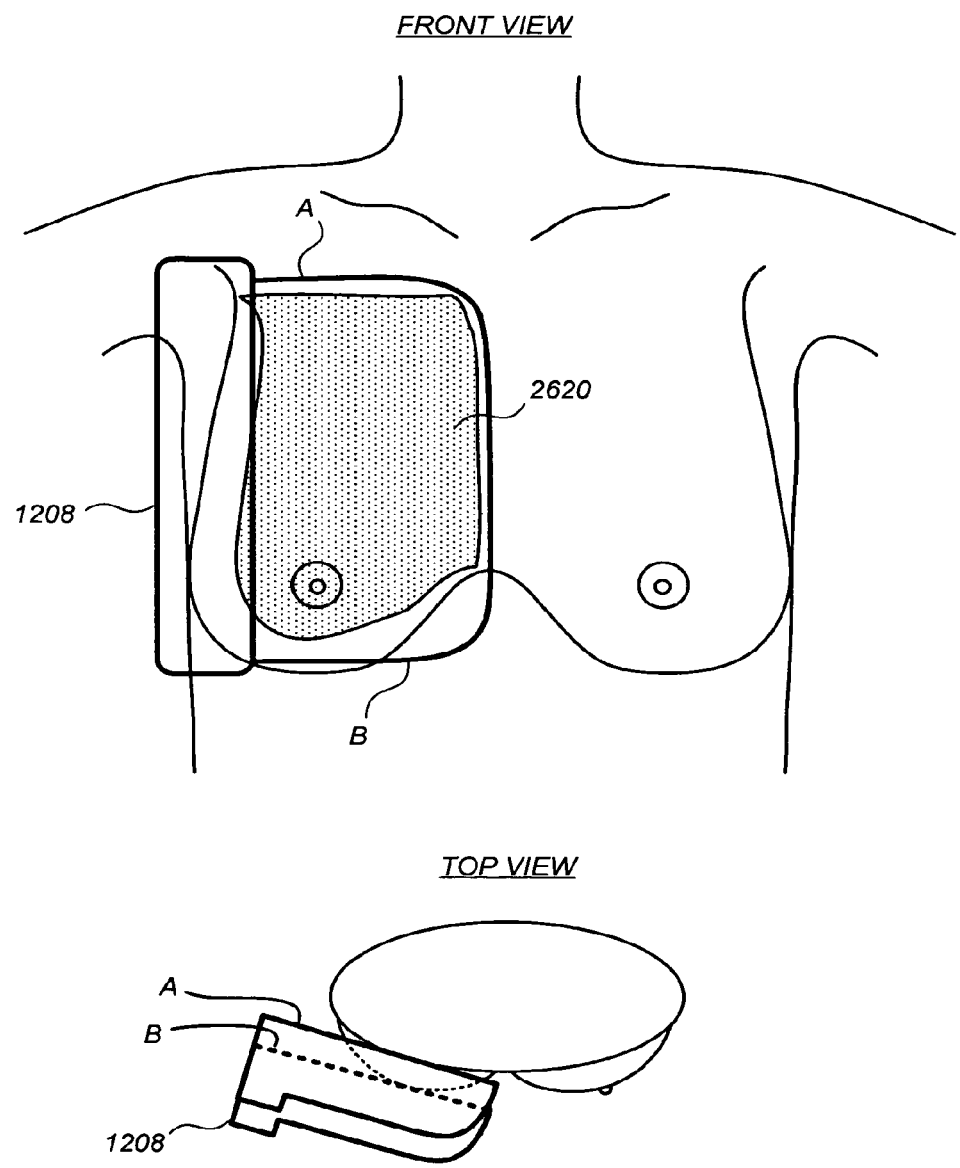
FIG. 26 illustrates a diagram of superior frontal breast ultrasound scanning according to a preferred embodiment.

FIG. 25 illustrates a diagram of inferior frontal breast ultrasound scanning according to a preferred embodiment, in which the compression/scanning assembly 1208 is manipulated to image an inferior frontal region 2518. In a manner analogous to the lateral and medial frontal scans, one side of the compressive surface is pinned at the inferior mammary fold (IMF, near the line C-C' in FIG. 25) and then the compressive surface is "rolled" upward toward the superior surface of the breast, until a position is reached in which the compressive surface would lift away from C-C' if the rolling continued. FIG. 26 illustrates a diagram of superior frontal breast ultrasound scanning according to a preferred embodiment, in which the compression/scanning assembly 1208 is manipulated to image a superior frontal region 2620.

In one embodiment, the number and selection of ancillary compressive scans is determined according to a size category of the breast. For a small breast, the lateral frontal scan (FIG. 23) and the medial frontal scan (FIG. 24) can suffice to ultrasonically image the clinically relevant tissues. For a medium sized breast, the inferior frontal scan (FIG. 25) is acquired in addition to the lateral and medial frontal scans to facilitate sufficient imaging of the clinically relevant tissues. For a large-sized breast, the superior frontal scan (FIG. 26) is acquired in addition to the lateral, medial, and inferior scans for capturing the clinically relevant tissues. Advantageously, a set of generally standard and comparable ultrasound image volumes is acquired according to the size of the breast for facilitating year-over-year comparisons, comparisons of similarly-sized breasts, and/or a variety of other useful purposes.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, while described supra in terms of having a membranous compression/scanning surface, in other preferred embodiments the compression/scanning surface can be a thin, rigid material such as polycarbonate plastic, or other materials that are described in U.S. Pat. No. 6,574,499, which is incorporated by reference herein. Therefore, reference to the details of the preferred embodiments are not intended to limit their scope, which is limited only by the scope of the claims set forth below.

What is claimed is:

1. An apparatus for ultrasonically scanning a breast of a patient, comprising:
    a hand-manipulable compressive member comprising a housing having an opening and an at least partially conformable membrane in a taut state, the membrane having a first surface compressing the breast in a generally chestward direction and a second surface opposite the first surface, the membrane positioned across the opening of the housing;
    an ultrasound transducer disposed within the housing;
    a transducer translation mechanism coupled to the ultrasound transducer and configured to sweep the ultrasound transducer across said second surface of said membrane to scan the breast while compressed in said generally chestward direction;
    a rigid and substantially stationary frame; and
    an arm pivotably mounted to said frame and to said hand-manipulable compressive member in a manner facilitating an orientation of said membrane in said generally chestward direction, the arm pivotably mounted to the housing at a side of the housing opposite the membrane and wherein the breast is only compressed by the first surface.

2. The apparatus of claim 1, said arm comprising first and second rigid members hingeably connected to each other, said first rigid member being pivotably mounted to said frame at a turret, said hand-manipulable compressive member being pivotably connected to said arm at a socket having ball-joint characteristics.

3. The apparatus of claim 2, wherein said first and second rigid members being hingeably connected provides for three translational degrees of freedom of said arm, and wherein said hand-manipulable compressive member being pivotably connected to said arm at said socket provides for three rotational degrees of freedom of said compressive member.

4. The apparatus of claim 1, wherein said hand-manipulable compressive member being pivotably connected to said arm in the manner facilitating the orientation of said membrane in said generally chestward direction comprises said hand-manipulable compressive member being pivotably connected to said arm in a manner to provide compression of the breast in the generally chestward direction while the patient is prone, standing upright, or supine.

5. The apparatus of claim 1, wherein said arm is configured to support the hand-manipulable compressive member to be neutrally buoyant in space or to have a light net downward weight for breast compression.

6. The apparatus of claim 1, further comprising a hand-held ultrasound system user interface rotatably mounted to a frame, said hand-held ultrasound system user interface including a display monitor and a handheld ultrasound probe.

7. The apparatus of claim 1, wherein the hand-manipulable compressive member is a first compressive member, and further comprising a second compressive member movable relative to the first compressive member to allow placement and compression of the breast therebetween, wherein:
    the first compressive member is movable to a first position to compress the breast in the generally chestward direction to accommodate head-on scanning of the breast by the ultrasound transducer; and
    the second compressive member is either completely removable from the apparatus or is movable to an out of the way position to allow positioning of the patient for said head-on scanning of the breast when said first compressive member is moved to said first position.

8. The apparatus of claim 1, wherein the membrane and the housing are optically transparent at locations that allow a user to view a surface of the breast during positioning and scanning.

9. The apparatus of claim 1, further comprising a position and orientation sensing system for providing compressive member position and orientation information.

10. The apparatus of claim 1, further comprising a lateral support element extending from the membrane toward the breast for lateral confinement of the breast during scanning, the lateral support element comprising an at least partially pliable material.

11. The apparatus of claim 1, wherein the hand-manipulable compressive member is configured to be placed into a first position for compressing the breast in the generally chestward direction when the patient is in a prone position, placed into a second position for compressing the breast in the generally chestward direction when the patient is standing upright, and placed into a third position for compressing the breast in the generally chestward direction when the patient is in a supine position.

12. A method for ultrasonically scanning a breast of a patient, comprising:
   compressing the breast between a hand-manipulable ultrasound scanning unit and a chest of the patient, the hand-manipulable ultrasound scanning unit comprising a substantially planar compressive surface positioned across a housing, the housing pivotably mounted to an arm at a side of the housing opposite the compressive surface, the arm pivotably mounted to a rigid and substantially stationary frame, the compressing performed by stationarily pressing the compressive surface of the hand-manipulable ultrasound scanning unit against the breast in a generally chestward direction; and
   sweeping an ultrasound transducer disposed within the housing of the hand-manipulable ultrasound scanning unit across the planar compressive surface to scan the breast therethrough while said compressive surface is stationarily pressed against the breast.

13. The method of claim 12, wherein said compressive surface comprises an at least partially conformable membrane in a substantially taut state, the breast compressed on only one side of the breast during the sweeping.

14. The method of claim 12, wherein said compressive surface is stationarily pressed against the breast in a head-on orientation substantially parallel to a coronal plane during said scan.

15. The method of claim 12, wherein said compressive surface is stationarily pressed against the breast in one of a lateral frontal orientation, a medial frontal orientation, an inferior frontal orientation, and a superior frontal orientation during the scan.

16. The method of claim 12, further comprising:
   categorizing the breast according to a size thereof;
   compressing the breast with a lateral frontal orientation and a medial frontal orientation of the compressive surface if the breast is of an at least small size;
   compressing the breast with an inferior frontal orientation of the compressive surface if the breast is of an at least medium size; and
   compressing the breast with a superior frontal orientation of the compressive surface if the breast is of a large size.

17. A method for ultrasonically scanning a breast of a patient, comprising:
   compressing the breast between a hand-manipulable ultrasound scanning unit and a chest of the patient, the hand-manipulable ultrasound scanning unit comprising a substantially planar compressive surface positioned across a housing, the compressing performed by stationarily pressing the compressive surface of the hand-manipulable ultrasound scanning unit against the breast in a generally chestward direction;
   sweeping an ultrasound transducer disposed within the housing of the hand-manipulable ultrasound scanning unit across the planar compressive surface to scan the breast therethrough while said compressive surface is stationarily pressed against the breast;
   categorizing the breast according to at least one criterion affecting a volumetric scanning efficacy when the compressive surface is stationarily pressed against the breast in a head-on orientation substantially parallel to a coronal plane in a head-on orientation; and
   if the volumetric scanning efficacy is below a predetermined threshold, performing said stationarily pressing for at least one ancillary orientation selected from the group consisting of: a lateral frontal orientation, a medial frontal orientation, an inferior frontal orientation, and a superior frontal orientation.

* * * * *